US005998588A

United States Patent [19]
Hoffman et al.

[11] Patent Number: 5,998,588
[45] Date of Patent: Dec. 7, 1999

[54] INTERACTIVE MOLECULAR CONJUGATES

[75] Inventors: Allan S. Hoffman; Patrick S. Stayton, both of Seattle, Wash.

[73] Assignee: University of Washington, Seattle, Wash.

[21] Appl. No.: 08/697,904

[22] Filed: Aug. 30, 1996

Related U.S. Application Data

[60] Provisional application No. 60/003,148, Sep. 1, 1995.

[51] Int. Cl.$^6$ .............................. C07K 17/08; A61K 3/74; A61K 39/385; A61K 39/395
[52] U.S. Cl. ........................ 530/402; 530/350; 530/387.1; 530/391.1; 530/395; 530/399; 530/403; 530/404; 530/405; 530/406; 424/78.08; 424/178.1; 424/193.1; 424/280.1; 424/94.1
[58] Field of Search ................................. 530/350, 387.1, 530/391.1, 395, 399, 402, 403, 404, 405, 406; 424/78.01, 178.1, 193.1, 280.1, 94.1

[56] References Cited

U.S. PATENT DOCUMENTS

| | | |
|---|---|---|
| 4,609,707 | 9/1986 | Nowinski . |
| 4,752,638 | 6/1988 | Nowinski . |
| 4,780,409 | 10/1988 | Monji et al. . |
| 4,783,409 | 11/1988 | Tosa et al. . |
| 4,839,293 | 6/1989 | Cantor et al. . |
| 4,843,010 | 6/1989 | Nowinski . |
| 4,946,778 | 8/1990 | Ladner et al. . |
| 4,971,905 | 11/1990 | Holmes . |
| 5,013,669 | 5/1991 | Peters . |
| 5,053,228 | 10/1991 | Mori . |
| 5,112,770 | 5/1992 | Carbonell . |
| 5,135,876 | 8/1992 | Andrade et al. . |
| 5,168,049 | 12/1992 | Meade et al. . |
| 5,226,902 | 7/1993 | Bae et al. . |
| 5,417,983 | 5/1995 | Nagase et al. ........................... 424/487 |
| 5,753,261 | 5/1998 | Fernandez et al. ...................... 424/450 |

FOREIGN PATENT DOCUMENTS

| | | |
|---|---|---|
| 469681 | 5/1992 | European Pat. Off. . |
| WO 86/01902 | 3/1986 | WIPO . |

OTHER PUBLICATIONS

Orlandi et al., *Proc. Natl. Acad. Sci. USA* 86:3833–3837 (1989).
Paganelli et al., *Int. J. Cancer* 45:1184–1189 (1990).
Sambrook et al., *Molecular Cloning: A Laboratory Manual*, 2d Ed., Cold Spring Harbor Laboratory Press, Cold Spring Harbor, NY (1989).
Sano et al., *Bio/Tech.* 11:201– (1993).
Takei, Y.G., et al., "Temperature–responsive Bioconjugates. 2. Molecular Design for Temperature–modulated Bioseparations", *Bioconj. Chem.*, 4:341–346 (1993).
Walter et al., *Anal. Biochem.* 197:1–18 (1991).
Yarmush et al., *Biotechnol. Prog.* 8:168–178 (1992).
Achari et al., *Biochemistry* 31:10449–10457 (1992).
Akerstrom and Bjorck, *J. Biol. Chem.* 261:10240–10247 (1986).
Alexander et al., *Biochemistry* 31:3597–3603 (1992).
Bird et al., *Science* 242:423–426 (1988).
Burns et al., *J. Org. Chem.* 56:2648–2650 (1991).
Chen, et al., *Biomaterials* 11(9), 625–630 (Nov. 1, 1990).
Chen, et al. *Biomaterials*, 11(9), 631–634 (Nov. 1, 1990).
Chen, G.H. and A.S. Hoffman, "A new temperature–+and pH–responsive Copolymer for Possible Use in Protein Conjugation", *Macromol. Chem. Phys.*, 196:1251–1259 (1995).
Chen, G.H., and A.S. Hoffman, "Preparation and Properties of Thermo–Reversible, Phase–Separating Enzyme–Oligo(NIPAAm) Conjugates", *Bioconj. Chem.* , 4:509–514 (1993).
Chen and Hoffman, "Synthesis of Carboxylated poly(NIPAAm) Oligomers and Their Application to Form Thermo–Reversible Polymer–enzyme Conjugates," *J. Biomaterials Sci. Polymer Ed*. 5:371–382 (1994).
Chen, G.H., and A.S. Hoffman, *Nature* 373:49–52 (1995).
Chen et al., *ACS Polymer Preprints* 33(2):468–469 (1992).
Chilkoti, A., et al., "Engineered Chimeric Streptavidin Tetramers as Novel Tools for Bioseparations and Drug Delivery," *Biotechnology* 13:1198–1204 (1995).
Chilkoti, A., et al., "Site–Specific Conjugation of a Temperature–Sensitive Polymer to a Genetically–Engineered Protein", *Bioconj. Chem.*, 5:504–507 (1994).
Chilkoti, et al. *Biocon. Chem.* 5(6), 504–507 (Nov.–Dec. 1994).
Ciardelli, *Biopolymers* 23:1423–1437 (1984).
Davis et al., *Bio/Technol.* 9:165–169 (1991).
Derrick and Wigley, *Nature* 359:752–754 (1992).
Ding, Z.L., G.H. Chen, and A.S. Hoffman, "Synthesis and Purification of Thermally–Sensitive Oligomer–Enzyme Conjugates of Poly(NIPAAm)–Trypsin", *Bioconj. Chem.*, 7:121–125 (1995).

(List continued on next page.)

*Primary Examiner*—Ponnathapura Achutamurthy
*Attorney, Agent, or Firm*—Arnall Golden & Gregory, LLP

[57] ABSTRACT

The combination of the capabilities of stimuli-responsive components such as polymers and interactive molecules to form site-specific conjugates which are useful in a variety of assays, separations, processing, and other uses is disclosed. The polymer chain conformation and volume can be manipulated through alteration in pH, temperature, light, or other stimuli. The interactive molecules can be biomolecules like proteins or peptides, such as antibodies, receptors, or enzymes, polysaccharides or glycoproteins which specifically bind to ligands, or nucleic acids such as antisense, ribozymes, and aptamers, or ligands for organic or inorganic molecules in the environment or manufacturing processes. The stimuli-responsive polymers are coupled to the recognition biomolecules at a specific site so that the polymer can be manipulated by stimulation to alter ligand-biomolecule binding at an adjacent binding site, for example, the biotin binding site of streptavidin, the antigen-binding site of an antibody or the active, substrate-binding site of an enzyme. Binding may be completely blocked (i.e., the conjugate acts as an on-off switch) or partially blocked (i.e., the conjugate acts as a rheostat to partially block binding or to block binding only of larger ligands). Once a ligand is bound, it may also be ejected from the binding site by stimulating one (or more) conjugated polymers to cause ejection of the ligand and whatever is attached to it. Alternatively, selective partitioning, phase separation or precipitation of the polymer-conjugated biomolecule can be achieved through exposure of the stimulus-responsive component to an appropriate environmental stimulus.

22 Claims, 12 Drawing Sheets

OTHER PUBLICATIONS

Fujimura, M., T. Mori and T. Tosa, "Preparation and Properties of Soluble–Insoluble Immobilized Proteases", *Biotech. Bioeng.*, 29:747–752 (1987).

Galaeu et al., J. Chromat., 684:37–43 (1994).

Green, *Meth. Enzymol.* 184:51–67 (1990).

Gronenborn et al., *Science* 253:657–661 (1991).

Harboe et al., *J. Clin. Microbiol.* 28:913–921 (1990).

Hendrickson et al., *Proc. Natl. Acad. Sci. USA* 86:2190–2194 (1989).

Heskins and Guillet, *J. Macromol. Sci.–Chem.* A2:1441–1455 (1968).

Hoffman, A.S., "Intelligent Polymers in Medicine and Biotechnology", *Artif. Organs*, 19:458–467 (1995).

Hoffman, A.S., "Intelligent Polymers in Medicine and Biotechnology", *Macromol. Symp.*, 98:645–664 (1995).

Irie, M., "Light–induced Reversible Conformational Changes of Polymers in Solution and Gel Phase", *ACS Polym. Preprints*, 27(2):342–343 (1986).

Irie, M. and D. Kungwatchakun, "Photoresponsive Polymers. Mechanochemistry of Polyacrylamide Gels having Triphenylmethane Leuco Derivatives", *Maokromol. Chem., Rapid Commun.*, 5:829–832 (1985).

Katz and Siewierski, *J. Chromatogr.* 624:403–409 (1992).

Kungwatchakun and Irie, *Makromol. Chem., Rapid Commun.* 9: 243–246 (1988).

Mamada et al., *Macromolecules* 23:1517–1519 (1990).

Martin et al., *Meth. Enzymol.* 203:121–153 (1991).

Matsuaka, M., et al., "Effect of Molecular Architecture of Poly(N–isopropylacrylamide)–trypsin conjugates on Their Solution and Enzymatic Properties," *Bioconjugate Chem.* 7:96–101 (1996).

Matsukata, M., et al., "Temperature Modulated Solubility–Activity Alterations for Poly(N–Isopropylacrylamide)–Lipase Conjugates", *J. Biochem.*, 116:682–686 (1994).

Meyer et al., *Exp. Hematol.* 19:710–713 (1991).

Miura et al., *Abstr. 17th Ann. Meet. Soc. Biomaterials* (1991).

Miura et al., J. Biomater. Sci. Polymer Edn, 5(6):555–568 (1994).

Monji, N. C.A. Cole, and A. S. Hoffman, "Activated, N–Substituted Acrylamide Polymers for Antibody Coupling: Application to a Novel Membrane–Based Immunoassay", *J. Biomtls. Sci. Polymer Ed.*, 5:407–420 (1994).

Monji, N., et al., "Application of a Thermally–Reversible Polymer–Antibody Conjugate in a Novel Membrane–Based Immunoassay", *Biochem. and Biophys. Res. Comm.*, 172(2):652–660 (1990).

Monji, N. and A.S. Hoffman, "A Novel Immunoassay System and Bioseparation Process Based on Thermal Phase Separating Polymers", *Appl. Biochem. and Biotech.*, 14:107–120 (1987).

Nguyen, A.L. and J.H.T. Luong, "Synthesis and Applications of Water–Soluble Reactive Polymers for Purification and Immobilization of Biomolecules", *Biotech. Bioeng.*, 34:1186–1190 (1989).

Osada, Y. and S.B. Ross–Murphy, "Intelligent Gels", *Sci. Amer.*, 268:82–87 (1993).

Otsu, T., et al. (1992) *Eur. Polym. J.*, 28:1325–1329).

Padlan and Kabat, *Meth. Enzymol.* 203:3–21 (1991).

Park, T. G. and A. S. Hoffman, "Synthesis and Characterization of a Soluble, Temperature–Sensitive Polymer–Conjugated Enzyme", *J. Biomtls. Sci. Polymer Ed.*, 4:493–504 (1993).

Phillips et al., *Science* 250:1130–1132 (1990).

Priest et al., *ACS Symposium Series* 350:255–264 (1987).

Sandmaier et al., *Blood* 76:630–635 (1990).

Shimoboji et al., Fifth World Biomaterials Congress May 29–Jun. 6, 1996.

Stappert et al., *Nucleic Acid. Res.* 20:624, (1992).

Stayton, P.S., et al., "Control of Protein–Ligand Recognition Using a Stimuli–Responsive Polymer", *Nature*, 378:472–474 (1995).

Takei, Y.G., et al., "Temperature–responsive Bioconjugates. 3. Antibody–Poly(N–isopropylacrylamide) Conjugates for Temperature–Modulated Precipitations and Affinity Bioseparations", *Bioconj. Chem.*, 5:577–582 (1994).

Takei, Y.G. et al., "Temperature–responsive Bioconjugates. 1. Synthesis of Temperature–Responsive Oligomers with Reactive End Groups and their Coupling to Biomolecules", *Bioconj. Chem.*, 4:42–46 (1993).

Tanaka, T., "Gels", *Sci. Amer.*, 244:124–138 (1981).

Taniguchi, M., M. Kobayahi and M. Fujii, "Properties of a Reversible Soluble–Insoluble Cellulase and Its Application to Repeated Hydrolysis of Crystallin Cellulose", *Biotech. Bioeng.*, 34:1092–1097 (1989).

Taylor and Cerankowski, *J. Polymer Sci.* 13:2551–2570 (1975).

Weber et al., *Science* 243:85–88 (1989).

Wilchek and Bayer, "Introduction to Avidin–Biotin Technology," *Methods in Enzymology* 184:5–45 (1990).

Wu et al., *Polymer* 33:4659–4662 (1992).

Zoller and Smith, *DNA* 3:479–488 (1984).

Bieth et al., *Proc. Natl. Acad. Sci. USA* 64:1103–1106 (1969).

Deziel & Mau, *Anal. Biochem.* 190:297–303 (1990).

Diamond and Hsu, *Adv. Biochem. Eng. Biotechnol.* 47:89–135 (1992).

Ede et al., *Bioconj. Chem.* 5:373–376 (1994).

Gaetner et al., *Bioconj. Chem.* 5:333–338 (1994).

Geoghegan & Shroh, *Bioconj. Chem.* 3:138–146 (1992).

Hoffman, *Macromol. Symp.*, 98:645–664 (1995).

Husain & Bieniarz, *Bioconj. Chem.* 5:482–490 (1994).

Lohmann and Petrak, *CRC Crit. Rev. Therap. Drug Carrier Systems* 5:263 (1989).

Mian, *J. Mol. Biol.* 217:133–151 (1991).

Miura et al., *J. Biomat. Sci Polymer Ed.*, 5:555–568 (1994).

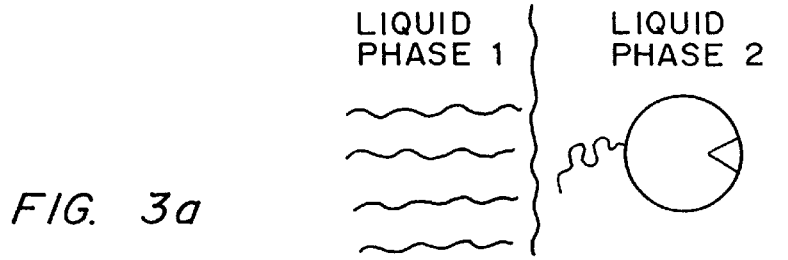
FIG. 3a
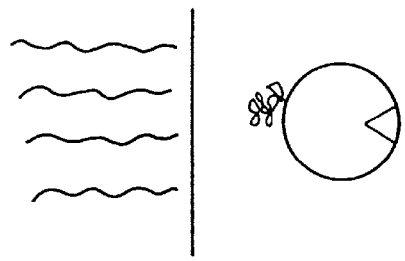
FIG. 3b
FIG. 3c
MORE COLLAPSED
THAN (a) BUT LESS
THAN OR SAME AS
(b)
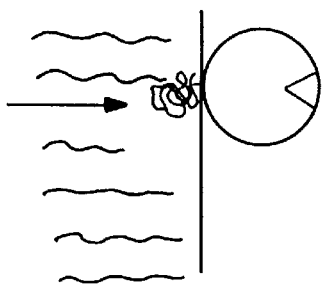
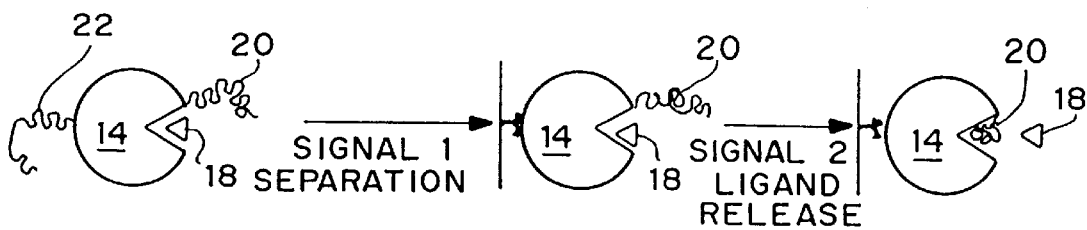
FIG. 4

1) NON-SPECIFIC ADSORPTION ("PHYSICAL" ADSORPTION = IONIC AND/OR HYDROPHOBIC FORCES)

2) AFFINITY ADSORPTION   OR

3) CHEMICAL COUPLING   OR

⊗ = -SH REACTIVE GROUP

MUTANT PROTEIN W/- SH GROUPS a1) PHYSICAL ADSORPTION
a2) AFFINITY ADSORPTION
a3) CHEMICAL COUPLING
⎯⎯⎯⎯⎯⎯⎯⎯⎯⎯
AS ABOVE

RESPONSIVE POLYMER

Random Copolymer of NIPAAm-AAc

TEMPORARY ENZYME INHIBITOR

∼ STIMULUS-RESPONSIVE POLYMER WHICH INHIBITS BINDING OF INHIBITOR

INACTIVE ENZYME          ACTIVE ENZYME

ABCVA

POLYMERIZATION CONDITIONS

TEMPERATURE : 60° C
    SOLVENT :     DMF
    TIME :     3 HOURS

ABCVA : 4,4-Azobis-4-cyanovaleric acid
DTDPA : 3,3'-Dithiodipropionic acid

INTERACTIVE MOLECULAR CONJUGATES

BACKGROUND OF THE INVENTION

This application claims priority to U.S. Ser. No. 60/003,148 filed Sep. 1, 1995 by Allan S. Hoffman and Patrick S. Stayton.

This application is generally in the area of molecular conjugates for use in affinity separations, drug delivery, sensors and other bioengineering applications.

There are many technologies, e.g. separations and sensors, which utilize a molecular recognition step as a key device component. These molecular recognition steps can be mediated by biomolecules or by synthetic receptors. Biological recognition processes have also been widely utilized in many clinical, industrial and laboratory applications, including bioseparations, cell culture, diagnostics, biosensors, targeted drug delivery, and enzyme and cell bioprocesses. They also have important new and potential uses in drug discovery, fundamental research in biological sciences and information processing. The central event in the recognition process involves the interaction or specific binding between a receptor and a ligand, such as the antibody-antigen binding reaction, or enzyme-substrate binding step, which is notable for its exceptional combination of specificity and affinity. The ability to control this binding step could not only lead to improvement in existing technologies but could also create entirely new applications in medicine, biotechnology, and industrial processing.

Protein conjugates with other molecules have long been used for protection of the protein from recognition, e.g., PEGylated proteins, targeting purposes and in separations and diagnostics technology, for example, streptavidin reactions and antibody-mediated affinity chromatography and antibody-enzyme conjugates, as in ELISA. Most of these are examples of non-site-specific conjugates, such as PEGylated proteins, antibody-drug bioconjugates and polymer-drug conjugates.

Polymers and small molecules have also been site-specifically conjugated to proteins for other purposes. For example, as reported by Chilkoti, et al. (1993), a stimuli-responsive polymer was site-specifically conjugated to a genetically engineered protein in order to precisely control the polymer:protein stoichiometry and to locate the polymer away from the protein active site, so that a physical phase separation could be carried out without interfering with the recognition site binding activity. Site-specific conjugation of polyethylene glycol to proteins via genetically-engineered cysteine residues has also recently been reported by Goodson and Kaktre, 1990; and Benhar, et al. 1994). These studies were designed to increase the circulation time and stability of therapeutic proteins without interfering with their activity, by assuring that the conjugated polymer was attached away from the active site. Polylysine polymers have also been conjugated to antibody fragments via existing thiol groups, in order to achieve better biodistribution and greater bioactivity of imaging and therapeutic antibodies, as reported by Slinkin, et al. 1992. Numerous examples of engineering cysteine residues for site-specific conjugation of small molecules, such as fluorophores or drugs, have been described by Stayton, et al. 1988). The photoswitchable binding of ligands to some protein binding sites via photochromic dye conjugation has also been reported by Willner and Rubin 1992; Willner et al. 1993. A photochromic dye that exists as two light-interconvertible isomers was conjugated randomly to protein lysine amino sites. Protein activity was shown to be dependent on the state of isomerization, so the protein could be switched between active and inactive forms by the photoisomerization of the dye. Concanavalin A binding to saccharides has been controlled by non-specific conjugation of several thiophenfulgide dyes to lysine residues (Willner and Rubin, 1992). The photoregulated activity of acetylcholinesterase and chymotrypsin via photochromic enzyme inhibitors has also been demonstrated by Bieth, et al. 1969.

Despite the recognition capabilities of proteins, technology based on protein catalysis, separations or delivery is often burdened by materials and processing costs. These drawbacks are related to the need to control several fundamental molecular processes such as protein recognition and binding to the target molecule, reaction kinetics, and separation and purification of the target molecule or its reaction by-product.

Current methods for controlling the sequential binding and release of target ligands in affinity-based technologies generally depend on the immobilization of the affinity agent on a solid surface, contact with a solution containing the target ligand and other species, to allow specific binding of the ligand to the affinity agent, and, for elution of a target ligand, the use of chemicals which are potential denaturants and/or solutions with large changes in pH or ionic strength. Processing steps are generally slow, requiring lengthy equilibration with large volumes of expensive buffer mixtures, and thus are often a primary hurdle in cost-effective separations. Non-specific binding of non-target molecules often contaminate the product. The need for advanced elution strategies in affinity-based techniques has been noted in the literature. (Yarmush et al., *Biotechnol. Prog.* 8:168–178 (1992)). Similarly, biosensor technologies (e.g., environmental or biological stream analysis) employing a protein-ligand detection system require elution of the bound target to regenerate the biosensor. Current immunoadsorbent, biosensor and chromatographic processing (e.g., elution) strategies would greatly benefit from a controlled, triggered release step providing faster response times and cleaner, purer and more concentrated separation streams.

There is a pressing need in the medical and processing industries for cost-effective isolation and delivery of therapeutic interactive molecules, rapid diagnostic strategies for preventive care, controlled and targeted delivery of therapeutic molecules, bioresponsive and biocompatible materials and careful control of enzyme-based processes. Similarly, cost-effective separations and diagnostic technologies are needed in the food, agriculture and marine industries, and for environmental testing and remediation.

It is therefore an object of the present invention to provide materials which can be used to modulate or "switch on or off" affinity or recognition interactions between molecules, for example, biological molecules, such as receptor-ligand interactions, enzyme-substrate interactions, and nucleic acid-complementary nucleic acid interactions, or by synthetic receptors such as host-guest complexes.

It is a further object of the present invention to provide methods for making and using these materials for processing, pharmaceutical and medical applications, and other technologies involving molecular binding.

SUMMARY OF THE INVENTION

The combination of the capabilities of stimulus-responsive components and interactive molecules to form site-specific conjugates which are useful in a variety of assays, separations, processing, and other uses is disclosed.

The polymers can be manipulated through alteration in pH, temperature, light, or other stimuli. The interactive molecules can be a biomolecule, such as (a) peptides or proteins, for example, antibodies, receptors, or enzymes, (b) polysaccharides or glycoproteins, or (c) nucleic acids such as antisense, ribozymes, and aptamers, all of which specifically bind to ligands or receptors, or a ligand for an organic or inorganic compound, for example, a metal chelating agent. The stimuli-responsive compounds are coupled to the interactive molecules at a specific site so that the stimulus-responsive component can be manipulated to alter ligand binding at an adjacent ligand binding site, for example, the antigen-binding site of an antibody or the active site of an enzyme. Binding may be completely blocked (i.e., the conjugate acts as an on-off switch) or partially blocked (i.e., the conjugate acts as a rheostat to partially block binding). Partial blocking can be used to effect selective binding, by still allowing small ligands to bind but totally blocking larger ligands.

These conjugates provide precise control of molecular interactions, for example, protein recognition steps or enzyme reaction steps in the processes by external signals, which avoid undesirable interferences or damage to the interactive molecules and targets during affinity binding, reaction (catalysis), or "unbinding" (separation). The interactive molecular conjugate systems are easy to adapt to a wide variety of separation, diagnostic, reaction, enzyme processes and delivery applications, and are economical to use.

Examples demonstrate formation of a site-specific conjugate by genetically engineering a protein, streptavidin, to insert a coupling site, then coupling a T-responsive polymer, polyNIPAAm, to the coupling site. The physical relationship (conformation) of the polymer to the biotin binding site of the streptavidin is controlled by altering the temperature of the reaction; i.e., at low temperatures, 100% of the biotin is bound, at higher temperatures, 37° C., significantly less biotin is bound.

BRIEF DESCRIPTION OF THE DRAWINGS

FIGS. 3a–c are schematic illustrations of an externally-triggered and reverse engineered polymer-protein conjugate designed for surface or interfacial or two phase partitioning separations. FIG. 3a shows the stimulus-interactive polymer in an unfolded or relaxed state. FIG. 3b shows the stimulus-interactive polymer in a collapsed form after exposure to a stimulus. FIG. 3c shows the same conjugate but with the stimulus-interactive polymer in an intermediate state between the uncollapsed or relaxed form of FIG. 3a and the completely collapsed form of FIG. 3b.

FIG. 4 is a schematic illustration of the combined affinity and partitioning switches, where signal 1 (a first stimulus) precipitates the polymer, directing an initial selective phase or interfacial partitioning, while signal 2 (a second stimulus) is used to release the ligand. A similar process may be used for phase separation and ligand release in two liquid phase systems as shown in FIG. 3.

DETAILED DESCRIPTION OF THE INVENTION

I. Stimulus Responsive-Interactive Molecular Conjugates

Stimulus-responsive components, most preferably polymers, and ligand-binding interactive molecules are combined to produce environmentally responsive interactive molecular conjugates. The stimulus-responsive component is attached to the interactive molecule at a site that affects the desired function of the interactive molecule, e.g., near the binding pocket of a ligand-receptor interaction. The functioning of the interactive molecule portion of the conjugate in recognition, complexation, reaction, separation, and delivery processes can then be controlled by a change in one or more external stimuli, such as temperature, pH, light, or electric field. The change causes the stimulus-responsive component to undergo a conformational or physico-chemical change which could lead to structural transition (e.g., collapse or precipitate, or the reversal thereof) at or near or distant (allostery) from the site of attachment, thereby modulating the activity of the interactive molecule in the process.

Figure 1A:
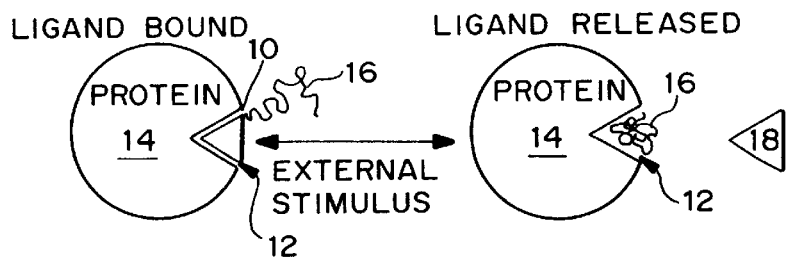
FIG. 1a is a schematic illustration of a stimulus-responsive polymer, site-specifically conjugated to a protein, that functions as a ligand affinity switch.

FIG. 1A is a schematic of a conjugate 10 of a stimulus-interactive molecule 16 bound to protein 14, where the stimulus-interactive molecule 16 blocks the binding site 12 of the protein 14 when not exposed to the stimulus and does not block the binding site 12 upon exposure to a stimulus, or vice versa. When the binding site 12 is not blocked, a ligand 18 can bind to the protein 14.

In the preferred embodiment, the stimuli-responsive components are synthetic or natural polymers that exhibit reversible conformational or physico-chemical changes such as folding/unfolding transitions, reversible precipitation behavior, or other conformational changes in response to changes in temperature, light, pH, ions or pressure.

Figure 1B:
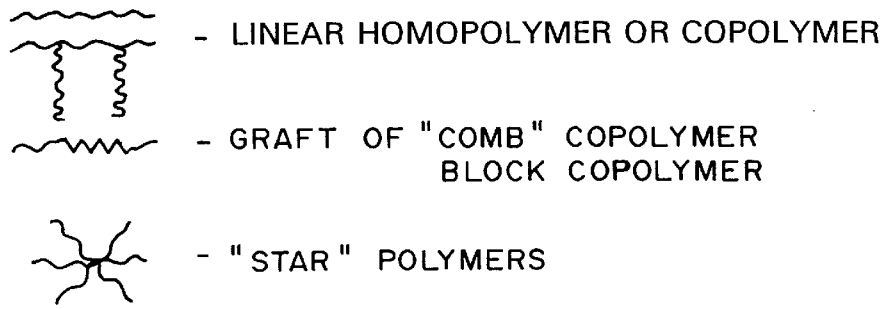
FIG. 1b is a schematic illustration of graft and block copolymers and random copolymers which enhance the stimulus response.

FIG. 1B are representative forms of the stimulus-interactive molecule 16 of FIG. 1A, including linear homo- or co-polymers, grafts of comb or block copolymers, and star polymers.

Figure 1C:
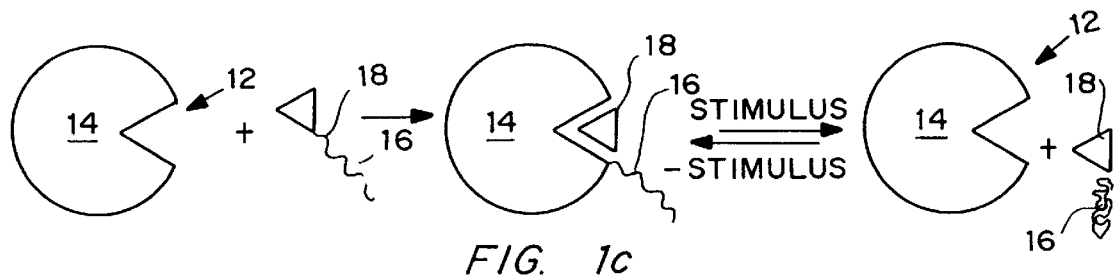
FIG. 1c is a schematic illustration of the ligand conjugate.

FIG. 1C is a schematic of an alternative embodiment, where the stimulus-responsive molecule 16 is bound to the ligand 18, which in the presence of a stimulus is blocked from binding to the binding site 12 of the protein 14, or vice versa.

Figure 1D:
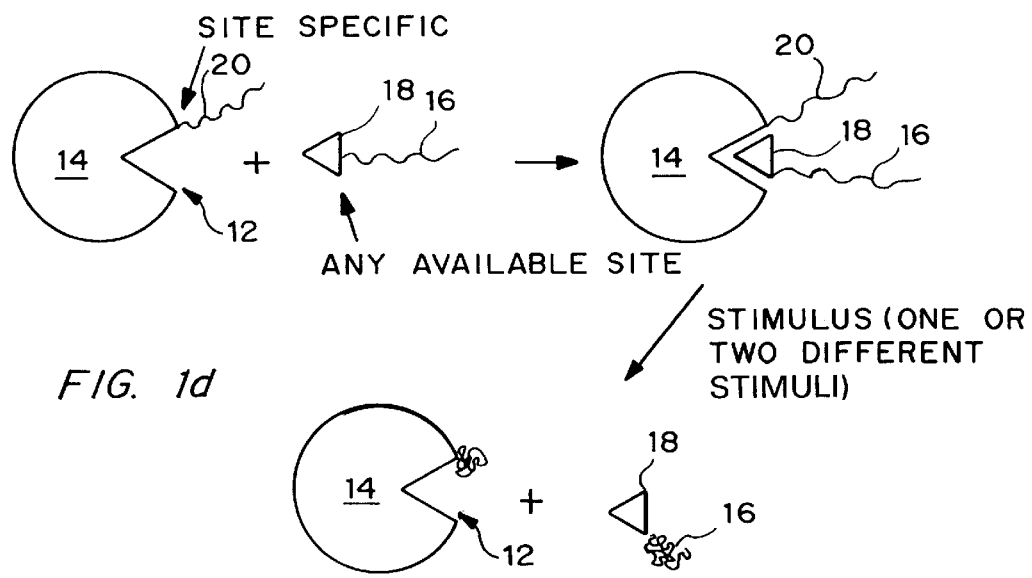
FIG. 1d is a schematic illustration of the combination of ligand-conjugate with receptor-conjugate.

FIG. 1D is a schematic of yet another embodiment, which is essentially a combination of the embodiments of FIGS. 1A and 1C. The protein 14 includes a stimulus-responsive polymer 20 which, upon exposure to a first stimulus, blocks the binding site 12. The ligand 18 is also conjugated to a stimulus-responsive polymer 16, which upon exposure to a second, different stimulus, blocks binding of the ligand 18 to the binding site 12. This provides a means for varying binding affinity as well as acting to prevent or allow binding.

1. Stimulus-responsive components

A number of polymers respond with large physical changes to small changes in environmental conditions, such as solution pH, ionic strength, solvent composition, temperature, light, and electric field. These polymers are referred to as stimuli-responsive, environmentally sensitive, "intelligent" or "smart" polymers. Hoffman, A. S., "Intelligent Polymers in Medicine and Biotechnology", *Macromol. Symp.*, 98, 645–664 (1995); also in: *Artif. Organs,* 19, 458–467 (1995).

Stimulus-responsive components useful to make the conjugates described herein can be any which are sensitive to a stimulus that cause significant conformational changes in the polymer coils, and which can be engineered to contain a group which is reactive with specific groups (e.g., ligands) on the interactive molecule of interest. Illustrative polymers described herein are temperature-, pH-, ion- and/or light-sensitive polymers. Hoffman, A. S., "Intelligent Polymers in Medicine and Biotechnology", *Artif. Organs,* 19, 458–467 (1995); Chen, G. H. and A. S. Hoffman, "A new temperature- and pH-responsive copolymer for possible use in protein conjugation", *Macromol. Chem. Phys.,* 196, 1251–1259 (1995); Irie, M. and D. Kungwatchakun, "Photoresponsive Polymers. Mechanochemistry of Polyacrylamide Gels having Triphenylmethane Leuco Derivatives", *Maokromol. Chem., Rapid Commun.,* 5, 829–832 (1985); and Irie, M., "Light-induced Reversible Conformational Changes of Polymers in Solution and Gel Phase", *ACS Polym. Preprints,* 27(2), 342–343 (1986); which are incorporated by reference herein.

Stimuli-responsive oligomers and polymers useful in the conjugates described herein can be synthesized that range in molecular weight from about 1,000 to 30,000 Daltons, with a reactive group at one or both chain ends. In a preferred embodiment, these syntheses are based on the chain transfer-initiated free radical polymerization of vinyl-type monomers, as described herein, and by (1) Tanaka, T., "Gels", *Sci. Amer.,* 244, 124–138 (1981); 2) Osada, Y. and S. B. Ross-Murphy, "Intelligent Gels", *Sci. Amer.,* 268, 82–87 (1993); (3) Hoffman, A. S., "Intelligent Polymers in Medicine and Biotechnology", *Artif. Organs,* 19, 458–467 (1995); also *Macromol. Symp.,* 98, 645–664 (1995); (4) Feijen, J., I. Feil, F. J. van der Gaag, Y. H. Bae and S. W. Kim, "Thermosensitive Polymers and Hydrogels Based on N-isopropylacrylamide", *11th European Conf. on Biomtls.,* 256–260 (1994); (5) Monji, N. and A. S. Hoffman, "A Novel Immunoassay System and Bioseparation Process Based on Thermal Phase Separating Polymers", *Appl. Biochem. and Biotech.,* 14, 107–120 (1987); (6) Fujimura, M., T. Mori and T. Tosa, "Preparation and Properties of Soluble-Insoluble Immobilized Proteases", *Biotech. Bioeng.,* 29, 747–752 (1987); (7) Nguyen, A. L. and J. H. T. Luong, "Synthesis and Applications of Water-Soluble Reactive Polymers for Purification and Immobilization of Biomolecules", *Biotech. Bioeng.,* 34, 1186–1190 (1989); (8) Taniguchi, M., M. Kobayahi and M. Fujii, "Properties of a Reversible Soluble-Insoluble Cellulase and Its Application to Repeated Hydrolysis of Crystalline Cellulose", *Biotech. Bioeng.,* 34, 1092–1097 (1989); (9) Monji, N., C-A. Cole, M. Tam, L. Goldstein, R. C. Nowinski and A. S. Hoffman, "Application of a Thermally-Reversible Polymer-Antibody Conjugate in a Novel Membrane-Based Immunoassay", *Biochem. and Biophys. Res. Comm.,* 172, 652–660 (1990); (10) Monji, N. C. A. Cole, and A. S. Hoffman, "Activated, N-Substituted Acrylamide Polymers for Antibody Coupling: Application to a Novel Membrane-Based Immunoassay", *J. Biomtls. Sci. Polymer Ed.,* 5, 407–420 (1994); (11) Chen, J. P. and A. S. Hoffman, "Polymer-Protein Conjugates: Affinity Precipitation of Human IgG by Poly(N-Isopropyl Acrylamide)-Protein A Conjugates", *Biomtls.,* 11, 631–634 (1990); (12) Park, T. G. and A. S. Hoffman, "Synthesis and Characterization of a Soluble, Temperature-Sensitive Polymer-Conjugated Enzyme, *J. Biomtls. Sci. Polymer Ed.,* 4,.493–504 (1993); (13) Chen, G. H., and A. S. Hoffman, Preparation and Properties of Thermo-Reversible, Phase-Separating Enzyme-Oligo(NIPAAm) Conjugates", *Bioconj. Chem.,* 4, 509–514 (1993); (14) Ding, Z. L., G. H. Chen, and A. S. Hoffman, "Synthesis and Purification of Thermally-Sensitive Oligomer-Enzyme Conjugates of Poly(NIPAAm)-Trypsin", *Bioconj. Chem.,* 7, 121–125 (1995); (15) Chen, G. H. and A. S. Hoffman, "A New Temperature- and pH-Responsive Copolymer for Possible Use in Protein Conjugation", *Macromol. Chem. Phys.,* 196, 1251–1259 (1995); (16) Takei, Y. G., T. Aoki, K. Sanui, N. Ogata, T. Okano, and Y.Sakurai, "Temperature-responsive Bioconjugates. 1. Synthesis of Temperature-Responsive Oligomers with Reactive End Groups and their Coupling to Biomolecules", *Bioconj. Chem.,* 4, 42–46 (1993); (17) Takei, Y. G., T. Aoki, K. Sanui, N. Ogata, T. Okano and Y. Sakurai, "Temperature-responsive Bioconjugates. 2. Molecular Design for Temperature-modulated Bioseparations", *Bioconj. Chem.,* 4, 341–346 (1993); (18) Takei, Y. G., M. Matsukata, T. Aoki, K. Sanui, N. Ogata, A. Kikuchi, Y. Sakurai and T. Okano, "Temperature-responsive Bioconjugates. 3. Antibody-Poly(N-isopropylacrylamide) Conjugates for Temperature-Modulated Precipitations and Affinity Bioseparations", *Bioconj. Chem.,* 5, 577–582 (1994); (19) Matsukata, M., Y. Takei, T. Aoki, K. Sanui, N. Ogata, Y. Sakurai and T. Okano, "Temperature Modulated Solubility-Activity Alterations for Poly(N-Isopropylacrylamide)-Lipase Conjugates", *J. Biochem.,* 116, 682–686 (1994); (20) Chilkoti, A., G. H. Chen, P. S. Stayton and A. S. Hoffman, "Site-Specific Conjugation of a Temperature-Sensitive Polymer to a Genetically-Engineered Protein", *Bioconj. Chem.,* 5, 504–507 (1994); and (21) Stayton, P. S., T. Shimoboji, C. Long, A. Chilkoti, G. Chen, J. M. Harris and A. S. Hoffman, "Control of Protein-Ligand Recognition Using a Stimuli-Responsive Polymer", *Nature,* 378, 472–474 (1995).

These types of monomers allow the design of copolymer compositions to respond to a specific stimulus and, in some embodiments, to two or more stimuli. In addition, control of molecular weight (by control of reactant concentrations and reaction conditions), composition, structure (e.g., linear homopolymer, linear copolymer, block or graft copolymer, "comb" polymers and "star" polymers, all of which may be incorporated into gel structure) and type and number of reactant end groups permit "tailoring" of the appropriate polymer for conjugation to a specific site on the interactive molecule. A genetically engineered temperature-sensitive peptide sequence may be constructed at the terminal end of the protein near or within the binding site. Peptide sequences which are pH, light, temperature, or chemical sensitive have also been reported and may be used to control the molecular recognition step via conjugation to the receptor or ligand, or through genetic incorporation into protein receptors or enzymes.

a. Temperature-responsive Polymers

Illustrative embodiments of the many different types of temperature-responsive polymers which may be conjugated to interactive molecules are polymers and copolymers of N-isopropyl acrylamide (NIPAAm). PolyNIPAAm is a thermally sensitive polymer that precipitates out of water at 32° C., which is its lower critical solution temperature (LCST), or cloud point (Heskins and Guillet, *J. Macromol. Sci.-Chem.* A2:1441–1455 (1968)). When polyNIPAAm is copolymerized with more hydrophilic comonomers such as acrylamide, the LCST is raised. The opposite occurs when it is copolymerized with more hydrophobic comonomers, such as N-t-butyl acrylamide. Copolymers of NIPAAm with more hydrophilic monomers, such as AAm, have a higher LCST, and a broader temperature range of precipitation, while copolymers with more hydrophobic monomers, such as N-t-butyl acrylamide, have a lower LCST and usually are more likely to retain the sharp transition characteristic of PNIPAAm (Taylor and Cerankowski, *J. Polymer Sci.* 13:2551–2570 (1975); Priest et al., *ACS Symposium Series* 350:255–264 (1987); and Heskins and Guillet, *J. Macromol. Sci.-Chem.* A2:1441–1455 (1968), the disclosures of which are incorporated herein). Copolymers can be produced having higher or lower LCSTs and a broader temperature range of precipitation.

Stimuli-responsive polymers such as poly(NIPAAm) have been conjugated randomly to affinity molecules, such as monoclonal antibodies, for example, as described in U.S. Pat. No. 4,780,409; Monji and Hoffman, *Appl. Biochem. Biotechnol.* 14:107–120 (1987). Activated groups (e.g, for conjugating to proteins), were formed randomly along the backbone of PNIPAAm and were conjugated randomly to lysine amino groups on a monoclonal antibody and the conjugate was then applied in a temperature-induced phase-separation immunoassay. Activated PNIPAAm has also been conjugated by Hoffman and coworkers to protein A, various enzymes, biotin, phospholipids, RGD peptide sequences, and other interactive molecules. The random polymer-interactive molecular conjugates have been used in a variety of applications based on the thermally-induced phase separation step (Chen and Hoffman, *Biomaterials* 11:631–634 (1990); Miura et al., *Abstr. 17th Ann. Meet. Soc. Biomaterials* (1991); Wu et al., *Polymer* 33:4659–4662 (1992); Chen and Hoffman, *Bioconjugate Chem.* 4:509–514 (1993); Morris et al., *J. Anal. Biochem.* 41:991–997 (1993); Park and Hoffman, *J. Biomaterials Sci. Polymer Ed.* 4:493–504 (1993); Chen and Hoffman, *J. Biomaterials Sci. Polymer Ed.* 5:371–382 (1994)). Others have also randomly conjugated proteins to PNIPAAm (Nguyen and Luong, *Biotech. Bioeng.* 34:1186–1190 (1989); Takei et al., *Bioconj. Chem.* 4:42–46 (1993)) and to pH-sensitive polymers (Fujimura et al., supra.)). Most of these polymer-protein conjugates involved random lysine amino groups of proteins bound to the polymer through random activated groups pendant along the polymer backbone. More recently, a new method based on chain transfer initiation polymerization has been used which yields relatively low MW polymers (called oligomers) usually with only one reactive end group (but the method may be adapted to synthesis of oligomers with a reactive group at each end) (Otsu, T., et al. (1992) *Eur. Polym. J.*, 28, 1325–1329). (Chen and Hoffman, 1993, supra; Chen and Hoffman, 1994, supra, and Takei et al., supra). The synthesis of an amino-terminated polymer proceeds by the radical polymerization of NIPAAm in the presence of AIBN as an initiator and 1-aminoethanethiol-hydrochloride as a chain transfer reagent. To synthesize a chain with —COOH or —OH terminal groups, carboxyl- or hydroxyl-thiol chain transfer agents, respectively, have been used instead of the amino-thiol. It should be noted that the synthesis of the end-reactive polymers is based on a chain transfer initiation and termination mechanism. This yields a relatively short polymer chain, having a molecular weight somewhere between 1000 and 25,000 to 30,000. The shortest chains, less than 10,000 in molecular weight, are usually called "oligomers". Oligomers of different molecular weights can be synthesized by simply changing the ratio of monomer to chain transfer reagent, and controlling their concentration levels, along with that of the initiator.

Oligomers of Vinyl Monomers

Oligomers of NIPAAm (or other vinyl monomers) having a reactive group at one end are prepared by the radical polymerization of NIPAAm using AIBN as initiator, plus a chain transfer agent with a thiol (—SH) group at one end and the desired "reactive" group (e.g., —OH, —COOH, —$NH_2$) at the other end. Chen and Hoffman, *Bioconjugate Chem.* 4:509–514 (1993) and Chen and Hoffman, *J. Biomaterials Sci. Polymer Ed.* 5:371–382 (1994), each of which is incorporated herein by reference. Appropriate quantities of NIPAAm, AIBN and chain transfer reagent in DMF are placed in a thick-walled polymerization tube and the mixtures are degassed by freezing and evacuating and then thawing (4 times). After cooling for the last time, the tubes are evacuated and sealed prior to polymerization. The tubes are immersed in a water bath at 60° C. for 4 h. The resulting polymer is isolated by precipitation into diethyl ether and weighed to determine yield. The molecular weight of the polymer is determined either by titration (if the end group is amine or carboxyl) or by vapor phase osmometry (VPO). If a pH-sensitive oligomer or polymer is desired, then acidic monomers such as methacrylic acid or acrylic acid, maleic acid or anhydride, AMPS, or the phosphate ester monomers described above ("Phosmer") can be used, as can basic monomers, such as aminoethyl methacrylate (AEMA), or vinyl formamide, which can be hydrolysed to polyvinyl amine after polymerization.

The molecular weight of vinyl-type copolymers can be controlled by varying the concentration of the key reactants and the polymerization conditions. However, it is difficult to achieve molecular weights much above about 30 kD using synthesis of vinyl-based oligomers by chain transfer initiation. Further, since the amino-thiol chain transfer agent yields a broader molecular weight distribution than the hydroxyl or carboxyl thiols (which may be undesirable), the —COOH-terminated polymer can be synthesized and the —COOH end group converted to an amine group by activating with carbodiimide and coupling a diamine to the active ester group.

Temperature sensitive oligopeptides also may be incorporated into the conjugates.

b. pH-sensitive Polymers

Synthetic pH-sensitive polymers useful in making the conjugates described herein are typically based on pH-sensitive vinyl monomers, such as acrylic acid (AAc), methacrylic acid (MAAc), maleic anhydride (MAnh), maleic acid (MAc), AMPS (2-Acrylamido-2-Methyl-1-Propanesulfonic Acid), N-vinyl formamide (NVA), N-vinyl acetamide (NVA) (the last two may be hydrolysed to polyvinylamine after polymerization), aminoethyl methacrylate (AEMA), phosphoryl ethyl acrylate (PEA) or methacrylate (PEMA). PH-sensitive polymers may also be synthesized as polypeptides from amino acids (e.g., polylysine or polyglutamic acid) or derived from naturally- occurring polymers such as proteins (e.g., lysozyme, albumin, casein, etc.), or polysaccharides (e.g., alginic acid, hyaluronic acid, carrageenan, chitosan, carboxymethyl cellulose, etc.) or nucleic acids, such as DNA. pH-responsive polymers usually contain pendant pH-sensitive groups such as —OPO$(OH)_2$, —COOH or —$NH_2$ groups. With pH-responsive polymers, small changes in pH can stimulate phase-separation, similar to the effect of temperature on solutions of PNIPAAm (Fujimura et al. *Biotech. Bioeng.* 29:747–752 (1987)). By randomly copolymerizing a thermally-sensitive NIPAAm with a small amount (e.g. less than 10 mole percent) of a pH-sensitive comonomer such as AAc, a copolymer will display both temperature and pH sensitivity. Its LCST will be almost unaffected, sometimes even lowered a few degrees, at pHs where the comonomer is not ionized, but it will be dramatically raised if the pH-sensitive groups are ionized. When the pH-sensitive monomer is present in a higher content, the LCST response of the temperature sensitive component may be "eliminated" (e.g., no phase separation seen up to and above 100° C.). On the other hand, graft and block copolymers of pH and temperature sensitive monomers can be synthesized which retain both pH and temperature transitions independently. Chen, G. H., and A. S. Hoffman, *Nature*, 373, 49–52 (1995).

C. Light-sensitive Polymers

Light-responsive polymers usually contain chromophoric groups pendant to or along the main chain of the polymer and, when exposed to an appropriate wavelength of light, can be isomerized from the trans to the cis form, which is dipolar and more hydrophilic and can cause reversible polymer conformational changes. Other light sensitive compounds can also be converted by light stimulation from a relatively non-polar hydrophobic, non-ionized state to a hydrophilic, ionic state. It is also possible to incorporate multiple environmental sensitivities in the same polymer, such as temperature and light sensitivity, by copolymerization.

In the case of pendant light-sensitive group polymers, the light-sensitive dye, such as aromatic azo compounds or stilbene derivatives, may be conjugated to a reactive monomer (an exception is a dye such as chlorophyllin, which already has a vinyl group) and then homopolymerized or copolymerized with other conventional monomers, or copolymerized with temperature-sensitive or pH-sensitive monomers using the chain transfer polymerization as described above. The light sensitive group may also be conjugated to one end of a different (e.g., temperature-) responsive polymer. A number of protocols for such dye-conjugated monomer syntheses are known. Kungwatchakun and Irie, supra, and Mamada et al., supra.

Although both pendant and main chain light sensitive polymers may be synthesized and are useful compositions for the methods and applications described herein, the preferred light-sensitive polymers and copolymers thereof are typically synthesized from vinyl monomers that contain light-sensitive pendant groups. Copolymers of these types of monomers are prepared with "normal" water-soluble comonomers such as acrylamide, and also with temperature- or pH-sensitive comonomers such as NIPAAm or AAc.

Light-sensitive compounds may be dye molecules that isomerize or become ionized when they absorb certain wavelengths of light, converting them from hydrophobic to hydrophilic conformations, or they may be other dye molecules which give off heat when they absorb certain wavelengths of light. In the former case, the isomerization alone can cause chain expansion or collapse, while in the latter case the polymer will precipitate only if it is also temperature-sensitive.

Light-responsive polymers usually contain chromophoric groups pendant to the main chain of the polymer. Typical chromophoric groups that have been used are the aromatic diazo dyes (Ciardelli, *Biopolymers* 23:1423–1437 (1984); Kungwatchakun and Irie, *Makromol. Chem., Rapid Commun.* 9:243–246 (1988); Lohmann and Petrak, *CRC Crit. Rev. Therap. Drug Carrier Systems* 5:263 (1989); Mamada et al., *Macromolecules* 23:1517 (1990), each of which is incorporated herein by reference). When this type of dye is exposed to 350–410 nm UV light, the trans form of the aromatic diazo dye, which is more hydrophobic, is isomerized to the cis form, which is dipolar and more hydrophilic, and this can cause polymer conformational changes, causing a turbid polymer solution to clear, depending on the degree of dye-conjugation to the backbone and the water solubility of the main unit of the backbone. Exposure to about 750 nm visible light will reverse the phenomenon. Such light-sensitive dyes may also be incorporated along the main chain of the backbone, such that the conformational changes due to light-induced isomerization of the dye will cause polymer chain conformational changes. Conversion of the pendant dye to a hydrophilic or hydrophobic state can also cause individual chains to expand or collapse their conformations. When the polymer main chain contains light sensitive groups (e.g. azo benzene dye) the light-stimulated state may actually contract and become more hydrophilic upon light-induced isomerization.

d. Specific Ion-Sensitive Polymers

Polysaccharides such as carrageenan that change their conformation, for example, from a random to an ordered conformation, as a function of exposure to specific ions such as $K^+$ or $Ca^{++}$, can also be used as the stimulus-responsive components. In another example, a solution of sodium alginate may be gelled by exposure to $Ca^{++}$. Other specific ion-sensitive polymers include polymers with pendant ion chelating groups, such as histidine or EDTA, etc.

e. Dual- or Multi-sensitivity Polymers

Figure 2A:
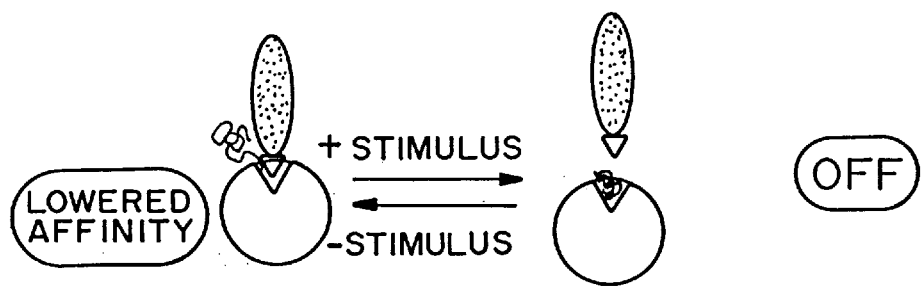
FIGS. 2a–d are schematic illustrations of four different modes of the affinity switch action of the responsive polymer-interactive molecular conjugate, with the ligand or recognition group of the ligand shown as the triangle. Unique functionalities, such as thiols, are located at selected sites within (FIGS. 2a and b) or near (FIG. 2c) the binding pockets or at distant sites structurally coupled or that can affect ligand binding to (FIG. 2d) the active site. Exposure of the conjugates to an appropriate stimulus results in binding or prevents binding, or which alters the binding site conformation, as in FIGS. 2C and 2D.
Figure 2B:
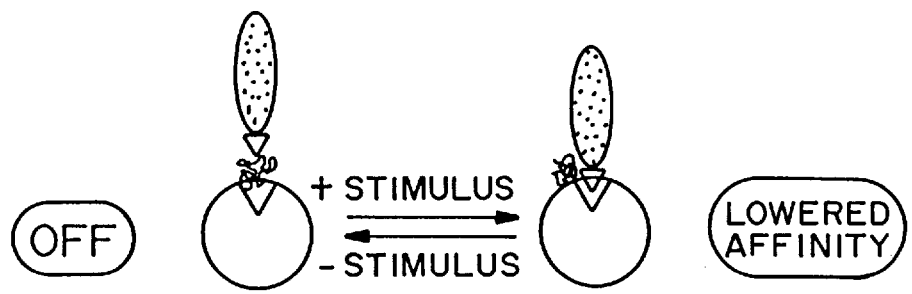
Figure 2C:
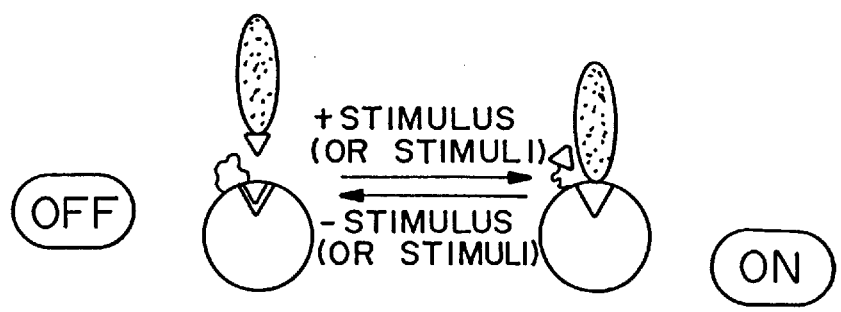

If a light-sensitive polymer is also thermally-sensitive, the UV- or visible light-stimulated conversion of a chromophore conjugated along the backbone to a more hydrophobic or hydrophilic conformation can also stimulate the dissolution or precipitation of the copolymer, depending on the polymer composition and the temperature. If the dye absorbs the light and converts it to thermal energies rather than stimulating isomerization, then the localized heating can also stimulate a phase change in a temperature-sensitive polymer such as PNIPAAm, when the system temperature is near the phase separation temperature. The ability to incorporate multiple sensitivities, such as temperature and light sensitivity, along one backbone by vinyl monomer copolymerization lends great versatility to the synthesis and properties of the responsive polymer-engineered protein conjugates. For example, dyes can be used which bind to protein recognition sites, and light-induced isomerization can cause loosening or detachment of the dye from the binding pocket (Bieth et al., *Proc. Natl. Acad. Sci. USA* 64:1103–1106 (1969)). This can be used for manipulating affinity processes by conjugating the dye to the free end of a temperature responsive polymer, such as ethylene oxide-propylene oxide (EO-PO) random copolymers available from Carbide. These polymers, —$(CH_2CH_2O)_x$—$(CH_2$—$CHCH_3$—$O)_y$—, have two reactive endgroups. The phase separation point can be varied over a wide range, depending on the EO/PO ratio, and one end may be derivatized with the ligand dye and the other end with an —SH reactive group, such as vinyl sulfone (VS). In this way, the VS reactive end of the polymer may be conjugated to a specific cysteine site located at a distance away from the binding pocket, such that the dye conjugated to the other end of the polymer is still able to reach and affinity bind in the pocket when the polymer conformation is in the expanded state. Then either a temperature stimulus or a combination of light and temperature stimuli may operate to remove the dye from the binding pocket, regenerating it for further affinity binding (or for enzymatic activity, if it is an enzyme). This mechanism is shown in FIG. 2c.

Random and Block Copolymers of EO/PO

Random copolymers of ethylene oxide (EO) and propylene oxide (PO) also have LCSTs or CPs ("Polyethylene Oxide," F. E. Bailey and J. V. Koleske Academic Press, NY (1976)) and have two reactive end groups, so they may be conjugated by one end to the engineered protein and other reactants, such as the light sensitive ligand depicted in FIG. 2C, may be conjugated to the other end. Temperature-sensitive block copolyethers are also available (from BASF). Triblocks of PEO-PPO-PEO are called Pluronics™ or poloxamers, and tetrablocks are called Tetronics™ or poloxamines. In the case of EO-PO random or block copolymers, a range of compositions, and molecular weights of these polymers having various reactive end groups can be obtained from Shearwater Polymers, Inc. (Huntsville, Ala.). The compositions are selected on the basis of data available on their cloud points. (BASF catalog, and "Polyethylene Oxide," F. E. Bailey and J. V. Koleske Academic Press, NY (1976)). A wider range of molecular weights of these copolyethers may be prepared than with the vinyl copolymers, since their synthesis does not use a free radical chain transfer initiation process.

Derivatization of End Groups

The reactive end group(s) of the oligomer is (are) then derivatized with specific groups (e.g., vinyl sulfone or maleimide) which are selectively reactive with the site-specific group to be conjugated (e.g., the thiol functionality of cysteine). To introduce maleimide or vinyl sulfone groups, an amine-terminated oligomer is preferred. The amine end group of the polymers may be conjugated with maleimide to provide thiol-reactivity (Chilkote et al., 1993). A hydroxyl-terminated polymer can be conjugated with vinyl sulfone by reaction with an excess of divinyl sulfone. The vinyl sulfone end group is typically more hydrolytically stable than the maleimide in conjugation reactions with protein thiol groups. Careful control of reactant stoichiometries and reaction conditions can yield bifunctional vinyl-type polymers such as polyNIPAAm or EO/PO random or block copolymers with different functional groups on each end of the polymer.

2. Interactive Molecules

The term "interactive molecule" as used herein includes any molecule capable of a specific binding interaction with a target site, for example on a cell membrane, or on a molecule or atom. Thus, interactive molecules include both ligands and receptors.

a. Selection of Interactive Molecules

The stimulus-responsive components can be conjugated to a variety of different interactive molecules, including peptides, proteins, poly- or oligo-saccharides, glycoproteins, lipids and lipoproteins, and nucleic acids, as well as synthetic organic or inorganic molecules having a defined bioactivity, such as an antibiotic or antiinflammatory agent, and which bind to a target site, for example on a molecule such as a cell membrane receptor. In one preferred embodiment the interactive molecule is a protein genetically engineered to insert a coupling site for the stimulus-responsive component at a desired site. Examples of protein interactive molecules are ligand-binding proteins, including antibodies, lectins, hormones, and receptors, and enzymes. Other molecules which bind specifically or non-specifically to a target molecule include poly- or oligosacharides on glycoproteins which bind to receptors, for example, the carbohydrate on the ligand for the inflammatory mediators P-selectin and E-selectin, and nucleic acid sequences which bind to complementary sequences, such as ribozymes, antisense, external guide sequences for RNAase P, and aptamers.

The interactive molecules are characterized by a binding site, which may be the active site of an antibody or enzyme, the binding region of a receptor, or other functionally equivalent site. These sites are collectively referred to as the binding site of the interactive molecule, unless specifically stated otherwise. As described below, the stimulus-responsive components are used to modify and/or manipulate binding of a target molecule to the binding site of the interactive molecule.

The number of proteins whose interaction with specific binding partners can be controlled via site-specific conjugation of a stimulus-responsive component is quite large. These include, for example, antibodies (monoclonal, polyclonal, chimeric, single-chain or other recombinant forms), their protein/peptide antigens, protein/peptide hormones, streptavidin, avidin, protein A, protein G, growth factors and their respective receptors, DNA-binding proteins, cell membrane receptors, endosomal membrane receptors, nuclear membrane receptors, neuron receptors, visual receptors, and muscle cell receptors. Oligonucleotides which can be modified include DNA (genomic or cDNA), RNA, antisense, ribozymes, and external guide sequences for RNAase P, and can range in size from short oligonucleotide primers up to entire genes. Carbohydrates include tumor associated carbohydrates (e.g., $Le^x$, sialyl $Le^x$, $Le^y$, and others identified as tumor associated as described in U.S. Pat. No. 4,971,905, incorporated herein by reference), carbohydrates associated with cell adhesion receptors (e.g. Phillips et al., Science 250:1130–1132 (1990)), and other specific carbohydrate binding molecules and mimetics thereof which are specific for cell membrane receptors.

In one embodiment, where the stimulus-responsive component is a polypeptide, it can be conjugated to the target interactive molecule, especially a protein, at a genetically engineered thiol attachment site, or genetically fused into the DNA sequence at an appropriate position relative to binding or active sites. (Angew. Chem. Int. Ed. Engl. 32, 819–841 (1993)).

Among the proteins, streptavidin is particularly useful as a model for other ligand-binding and substrate-binding systems described herein. Streptavidin is an important component in many separations and diagnostic technologies which use the very strong association of the streptavidin-biotin affinity complex. (Wilchek and Bayer, Avidin-Biotin Technology, New York, Academic Press, Inc. (1990); and Green, Meth. Enzymol. 184:51–67. Protein G, a protein that binds IgG antibodies (Achari et al., Biochemistry 31:10449–10457 (1992), and Akerstrom and Bjorck, J. Biol. Chem. 261:10240–10247 (1986)) is also useful as a model system. Representative immunoaffinity molecules include engineered single chain Fv antibody (Bird et al., Science 242:423–426 (1988) and U.S. Pat. No. 4,946,778 to Ladner et al., incorporated herein by reference, Fab, Fab', and monoclonal or polyclonal antibodies. Enzymes represent another important model system, as their activity can be turned on or off or modulated by the controlled collapse of the stimulus-responsive component at the active site.

In addition to their well established uses in biotechnology, streptavidin, protein G, single-chain antibodies and enzymes are ideal model systems for several other important reasons. Genetic engineering systems for these proteins have been established, allowing convenient site-directed mutagenesis and the expression of large quantities of each protein in hosts such as E. coli. High-resolution crystal structures are available that provide a molecular "road map" of the ligand binding sites (Achari et al. supra; Hendrickson et al., Proc. Natl. Acad. Sci. USA 86:2190–2194 (1989); Weber et al., Science 243:85–88 (1992); Derrick and Wigley, Nature 359:752–754 (1992); Mian, J. Mol. Biol. 217:133–151 (1991)). This structural information provides a rational basis for the design of affinity or activity switch site-directed mutants. Of course, proteins which already have one, two or more cysteine residues located at a site convenient for attaching a stimulus-responsive component are ready for attachment of the stimulus-responsive component and need not have other cysteine residues engineered therein (unless another thiol group is desired in a specific site or useless reaction of the wild type —SH group undesirably changes the protein bioactivity). Other sites on the proteins can also be used, including amino acids substituted with non-natural amino acids.

Synthetic genes that direct the high-level expression of core streptavidin and protein G in E. coli have been constructed. See, e.g., U.S. Pat. No. 4,839,293, incorporated herein by reference. The genes incorporate biased codon usage for E. coli to maximize expression, convenient restriction sites for cassette mutagenesis, an initiating methionine, and stop codons. The synthetic genes can incorporate favored E. coli codon usage to maximize expression, and several restriction enzyme sites can be incorporated at unique sites within the gene to facilitate mutagenesis efforts. The gene sequence encoding the form of protein G for which the NMR solution structure has been reported (Gronenborn et al., Science 253:657–661 (1991)) has also been constructed. A single-chain Fv antibody gene has also been cloned and constructed from the parent antibody S5, which recognizes the CD44 receptor antigen (Sandmaier et al., Blood 76:630–635 (1990)). Single-chain antibodies consist of the variable heavy and variable light chains connected by a short peptide linker, and are constructed by using polymerase chain reaction techniques to produce a single-chain Fv antibody(Bird et al., supra; Orlandi et al., *Proc. Natl. Acad. Sci. USA* 86:3833–3837 (1989); and Davis et al., *Bio/Technol.* 9:165–169 (1991)), each of which is incorporated herein by reference.

b. Selection or creation of Sites where Molecules are Bound

The stimulus-responsive components are covalently linked by their end groups to the molecules at one or more selected sites, generally referred to herein as "coupling sites", such that, once the stimulus-responsive component is attached to the molecule, the stimulus-responsive component coil remains in the soluble hydrated state. When the environmental signal or stimulus (or stimuli, depending on whether different stimulus-responsive components have been attached) is triggered, the stimulus-responsive component may become more hydrophobic and the stimulus-responsive component coil contracts and in some cases may "phase separate" (e.g., collapse) within or near the attachment site. In some cases, as with a light stimulus, the stimulus-responsive component may both contract and become more hydrophilic due to isomerization induced structural changes of a dye that is incorporated in the stimulus-responsive component.

Additionally, ion-sensitive stimulus-responsive components such as components capable of $Ca^{++}$ sensitive polymer conformational changes may be used. Additionally, single stranded DNA, one end of which is attached to a specific site on the interactive molecule, while the complementary sequence of base pairs is attached on one end of the stimulus-responsive component may be used, so that when the DNA pairs off, hooking the stimulus-responsive component to a specific site on the protein, the distance the smart stimulus-responsive component attachment is from the protein active site is controlled.

Typically the linkage site(s) will be (a) just outside the binding site of the molecule, (b) at selected distances away from the binding site, (c) just inside the binding sites, (d) deep inside the binding pockets, and/or (e) at a selected site at some distance from the binding site (f) at allosteric sites distant from the binding sites. When situated at a desired site near the binding site of the molecule, sufficient hindrance, steric or otherwise, is provided by the contracted or collapsed stimulus-responsive component to adversely affect the ligand binding equilibrium while minimally affecting the affinity of the ligand for the molecule's binding pocket or active site when the stimulus-responsive component is in the expanded state. Thus, upon stimulation, the conformational change or collapse of the polymer coil either inhibits, directly or allosterically, the entrance of the ligand to a protein binding pocket or an enzyme's active site and/or interferes with the ligand which is already bound within the site, thereby causing its complete expulsion from the binding pocket or a reduction in affinity. The polymer can also be engineered to gradually collapse, which allows the conformation of the polymer to be controlled, by gradual small, variations or changes in environment conditions, and thus the degree of reaction inhibition to be controlled over a range of intermediate affinities or reactivities. Recovery of the molecule's binding affinity or enzymatic activity can be effected by a return to the environmental conditions favoring the soluble, extended and hydrated random polymer coil. Alternatively, as shown in FIG. 2*b*, in some cases the hydrated coil can block the binding pocket more effectively than the collapsed coil. Additionally, there may be an advantage to using a pendant reactive group on the polymer backbone to provide better blocking of the binding site.

To determine the optimal combination of polymer and attachment site(s) for a desired response, polymer composition and molecular weight can be varied, as can the type and magnitude of the stimulus and the specific conjugation site or sites (e.g., two different or two similar stimulus-responsive components can be conjugated to two different sites). If the light-sensitive group is along the main chains, it may be shortened in the hydrophilic state by the isomerization of the dye.

Sites for covalent attachment of the stimulus-responsive component on the interactive molecule may already exist or can be created by a variety of techniques depending on the nature of the molecule. For example, if the molecule is a recognition protein that already contains a cysteine residue at a desired site, e.g., in or near an enzyme's active site, this native site can be used for attachment so long as conjugation of stimulus-responsive component to any other cysteine residues that may be present in the enzyme does not adversely affect the enzyme activity or the control exerted by the stimulus-responsive component at the active site. When the molecule is a protein or nucleic acid , recombinant DNA techniques can be used to provide a site if there is not one in the native molecule suitable for linking the stimulus-responsive component. Typically, a thiol side chain (e.g., one or more cysteine residues) is genetically engineered at a predetermined surface position at or near a ligand binding site of a protein, or at a distant site such as an allosteric site (depending on the desired action of the stimulus). Techniques such as site-specific mutagenesis can be used and are described by, for example, Zoller and Smith, *DNA* 3:479–488 (1984), Sambrook et al., *Molecular Cloning: A Laboratory Manual,* 2d Ed., Cold Spring Harbor laboratory Press, Cold Spring Harbor, NY (1989), and a useful polymerase chain reaction-mediated site-directed mutagenesis procedure is described by Stappert et al., *Nucleic Acid. Res.* 20:624, (1992). Similar techniques can also be used to remove undesired sites that may occur in a native or wild type protein. Other reactive amino acids can also be engineered and non-natural amino acids can also serve as unique attachment sites. When the affinity molecule is an oligonucleotide, thiolated oligonucleotides for stimulus-responsive component attachment can be inserted during synthesis, as described in Ede et al., *Bioconj. Chem.* 5:373–376 (1994), incorporated herein by reference. With synthetic interactive molecules, unique chemical hooks such as thiols, amines, or hydroxyls can be synthetically incorporated at appropriate positions near the recognition site.

The insertion sites are chosen so that the stimulation of the responsive stimulus-responsive component (or stimulus-responsive component-ligand conjugate) at that position changes the ligand-binding affinity in the desired manner. Two cysteine residues can be engineered near the binding site so that the affinity will be altered by the precipitation of two stimulus-responsive components near the binding site, or one cysteine residue is placed near the active site and one is placed within the interface between monomeric units of streptavidin, to provide a combined effect from the two acting together.

High-resolution X-ray crystallographic structures of the three proteins are used to determine appropriate positions for site-directed mutagenesis. With modeling techniques, positions are located with appropriate solvent-accessibility for reaction with the stimulus-responsive components, and positions deeper in the binding pocket are identified which require partial unfolding for conjugation. Sites are chosen at the subunit—subunit interfaces in streptavidin and the single-chain Fv antibody to allosterically reduce the affinity by changing the protein structure by stimulating a conformational change in the polymer conjugated at a distant site. Numerous sites both around the binding sites of the three proteins and at appropriate allosteric sites away from the binding site can be used where the binding affinity will be reduced by stimulus-responsive component precipitation.

The site may also be chosen to be a certain distance from the active site; then a ligand is conjugated at one end of the smart stimulus-responsive component and the other end is conjugated to the chosen distant site. An appropriate stimulus can lower the ligand affinity in the site and/or cause it to be pulled from the site; both actions may occur in some cases if the ligand-site affinity is affected by one stimulus and the stimulus-responsive component by a different stimulus, and the two stimuli are applied in sequence and/or simultaneously.

Once sites are chosen, cassette or PCR site-directed mutagenesis techniques are used to introduce cysteine residues at those positions. The engineered proteins are produced in *E. coli*, and then characterized, including CD characterization of secondary structure and binding affinity measurements, to confirm that the mutation itself has not adversely affected the protein structure, stability, and/or activity. The mutant proteins are then used for conjugation to the stimulus-responsive components as described below.

To facilitate placement of a stimulus-responsive component attachment site in or near the binding pocket or other desired site, site-directed binding pocket mutants can be produced to optimize the thermodynamic and kinetic properties specifically for use with stimulus-responsive components. Such mutants display altered ligand affinities and thus provide additional control over protein function for optimizing stimulus-responsive component-molecular conjugates. Libraries of site-directed affinity mutants can be used. For example, several ligand-binding site mutations have been constructed in streptavidin which alter important biotin-binding interactions, as described in copending U.S. application Ser. No. 08/387,055, incorporated herein by reference. This provides a choice for the initial ligand-binding thermodynamic properties, so that changes in affinity triggered by the stimulus-responsive component can be engineered to fall in a useful and desired range.

Depending on the stimulus-responsive component's composition, molecular weight and location of the conjugation site(s) on the molecule, environmental stimulus can be applied to affect: (a) the gradual or rapid and, if desired, reversible switching of molecular binding interactions on and off, (b) the partitioning or separation of the stimulus-responsive component-molecule conjugates (with or without their affinity targets) to selective surfaces, interfaces or second aqueous phases, and (c) a combination of (a) and (b), wherein the conjugates are first directed to a specific surface, interface, or phase, and then the bound ligand is "switched off" (released) to the local microenvironment. In case (c) the two steps may be reversed in sequence. By applying small changes in environmental stimuli, such as temperature and/or pH and/or light, to the system, one can achieve environmental control over the stimulus-responsive component-molecule microenvironment, which permits molecular level control of the recognition and binding capability of different size and composition ligands with affinity proteins or different size and composition substrates with enzymes, selectively controlling the specific bioactivity of the molecule. The change in stimulus-responsive component conformation can also expose or block the active site of an enzyme, whose action is to release a biochemical or chemical agent by enzymolysis of the agent's linkage to the smart stimulus-responsive component.

The attachment site for the stimulus-responsive components can thus be directed to well-defined positions relative to the ligand binding site of each protein. Cysteine conjugation sites can be readily engineered just outside the binding sites, at selected distances away from the binding site, just inside the binding sites, deep inside the binding pockets, and/or at potential allosteric sites distant from the binding sites.

For example, the streptavidin Asn 49 residue lies in a solvent accessible position on the border of the biotin binding site, and this residue has been mutated to cysteine (N49C) using site directed mutagenesis techniques. Large quantities of this protein have been expressed and purified, and a vinyl sulfone-modified poly(NIPAAm) temperature-responsive stimulus-responsive component has been conjugated to this position. Streptavidin does not contain cysteine in its native sequence, making it convenient to introduce unique thiol side-chains. To design an exemplary site-directed mutant aimed at controlling its recognition processes as described herein, the general criteria center on choosing a site near the biotin binding site with significant aqueous solution exposure at the atom where the thiol is substituted. One goal is to introduce a thiol with sufficient solvent exposure (to permit relative ease of conjugation to the responsive stimulus-responsive component), and at a site where the collapse of the stimulus-responsive component should sterically interfere with ligand binding. The biotin binding site of streptavidin is covered by a loop that is extremely flexible and disordered in the ligand-free state. This loop becomes ordered and forms a "lid" over the binding site when biotin is bound. This loop represents a target for stimulus-responsive component conjugation. The site-directed mutant places a cysteine at position 49 (Asn49Cys), which borders the lid.

Like streptavidin, protein G does not contain cysteine residues in the native structure. Protein G exists naturally as a multi-domain protein with high affinity for IgG antibodies and Fc derivatives. A small (55 amino acid) domain has been genetically constructed, which retains native affinity for IgG ($Ka>10^7M^{-1}$) and which displays extremely high stability and a highly reversible folding/unfolding equilibrium (Alexander et al., *Biochemistry* 31:3597–3603 (1992)). Co-crystal analysis suggests that protein G recognizes IgG by forming an antiparallel interaction between its second β-strand and the last β-strand of the antibody heavy chain C1 domain (Derrick and Wigley, *Nature* 359:752–754 (1992)), while a solution NMR study suggests that the helix is involved centrally. Thus, mutants have been made that introduced unique cysteine residues near both sites. Three initial cysteine mutants have been constructed, with the thiol side-chain introduced at positions 11, 21, and 37. All three proteins have been expressed and purified in large quantities for conjugation to thiol-specific stimulus-responsive components.

The primary amino acid sequences in the antibody family show a large degree of homology. The large library of high resolution, X-ray structures for crystallized antibodies has conclusively demonstrated that these primary sequence homologies translate into a highly conserved three-dimensional fold (Padlan and Kabat, *Meth. Enzymol.* 203:3–21 (1991)), even within the variable domains where most of the variability is confined to six well defined hypervariable loops that constitute the antigen binding contacts. The remainder of the variable domain consists of a highly conserved β-sheet framework that is responsible for the familiar antibody β-barrel fold. It is thus possible to generate a high resolution molecular model for single-chain antibodies of known sequence in the absence of X-ray crystal structure analysis (Martin et al., *Meth. Enzymol.* 203:121–153 (1991)), and several positions for introducing thiol side-chains can be identified.

c. Methods and Reagents for Conjugation

Optimal solution conditions are used for site-specifically conjugating molecules to the genetically-engineered cysteines. The chemically reactive nucleophile is the thiolate anion. It is thus important to keep the side-chain reduced and to optimize the conjugation pH. The pH and the stimulus-responsive component's activated end group must also be chosen so that the competing conjugation to the amino groups of lysine side-chains is avoided. The pH will also determine the rate of hydrolysis of the thiol-specific electrophilic functionality on the stimulus-responsive component. Conjugation reactions to —SH groups are typically conducted between pH 6 and 7.5, which is below the pH where lysine amino groups are most reactive. The protein-engineered cysteine thiol groups often cross-link spontaneously in solution, so that one begins with disulfide-bonded dimers of protein G. etc. These disulfides are reduced prior to conjugation using dithiothreitol, tris(2-carboxyethyl) phosphine (TCEP), or a similar reagent. TCEP does not react with the thiol-specific electrophiles, such as the vinyl sulfones to be used here, and can thus be used directly in the conjugation solution to ensure that the thiol is kept in the active oxidation state. Typical starting reaction conditions are 50 mM phosphate buffer, pH 7.0, 100–300 μM protein, 1 mM TCEP (added at least twice), 50-fold molar excess stimulus-responsive component (to protein), room temperature, 2 hours. Common variations are temperature and time (e.g. overnight at 4° C.).

d. Separation and Purification of Conjugate

The conjugation mixture is then passed over a SEPHADEX™ G-50 gel filtration column. The stimulus-responsive component-protein conjugate is separated from the unreacted protein by thermal precipitation of the stimulus-responsive component which brings the conjugates and any unreacted stimulus-responsive component out of solution. The conjugate and any unreacted stimulus-responsive component are then redissolved in buffer and characterized by SDS-PAGE electrophoresis. The conjugate is also characterized by HPLC analysis on a GPC column, where the conjugate runs at a different molecular weight than the free protein or stimulus-responsive component. MALDI-TOFS mass spectrometry techniques can also be used to characterize the conjugate, which provides high-resolution molecular weight analysis that is strong evidence of 1:1 stoichiometry. Control experiments are conducted with wild-type protein, where there is no conjugation of the stimulus-responsive component, to confirm the specificity of the conjugation to the genetically engineered cysteine of the mutant proteins. Peptide mapping can also be conducted to exactly characterize which residue (i.e. the engineered cysteine) has been modified..

e. Optimization of Conjugation Reaction

As the reactivity of engineered thiols can vary widely depending on their position on the protein surface, there are alternative reaction conditions to the basic protocol given above to increase the efficiency of the conjugation reaction. For example, the reaction efficiency is often increased greatly by adding protein denaturants at low concentrations. These denaturants unfold the protein slightly and increase the accessibility of the thiol functional groups. As outlined above, the length of reaction, temperature, and pH can also be varied to increase the efficiency of the conjugation reaction. In the above protocol, there is no separation of the unreacted stimulus-responsive component. In activity assays, a washing step can be used to remove excess stimulus-responsive component before quantitating the binding affinity. However, it is possible that the excess stimulus-responsive component would interfere somewhat with the initial binding step, and it may thus be desirable to remove the unreacted stimulus-responsive component. This is done with streptavidin and protein G by running the conjugation mixture over an affinity column. The streptavidin conjugates can be passed over a standard iminobiotin column so that the stimulus-responsive component-protein conjugate will bind, while any free stimulus-responsive component is washed through. Similarly, protein G can be passed over a commercial IgG affinity column, with the conjugate binding to the column and the stimulus-responsive component washed through. Ion-exchange chromatography can be used to separate conjugates with different stoichiometries if stimulus-responsive components have been conjugated to lysine residues in addition to the genetically engineered cysteine.

The stimulus responsive component may be coupled to the molecule using conjugation methods available in the art, and described for example, in Taylor, Ed., "Protein Immobilization", Marcel Dekker, New York, 1991; and Scouten, "Affinity Chromatography", J. Wiley % Sons, New York, 1981.

f. Linkers (Spacers) between Stimulus-responsive Component and Molecule.

Although the foregoing description has focused on direct binding of the stimulus-responsive component to the molecule, linkers or spacer groups can also be used to connect the stimulus-responsive component to the desired site on the molecule. Nucleic acids offer the additional advantage that they can be made complementary to a target and used for targeting as well as in combination with the stimulus-responsive component to regulate access to the binding site. In a preferred embodiment, the stimulus-responsive components can be attached to a protein via an intervening oligonucleotide which is complementary in sequence to an oligonucleotide that has been conjugated to a specific site on the engineered protein (FIG. 12). For example, an oligonucleotide can be site-specifically conjugated to an engineered protein thiol, and its complementary sequence conjugated to an end-reactive stimulus-responsive component. (The DNA may also be conjugated to a reactive pendant group along the stimulus-responsive component backbone). The base-pairing between the two complementary oligonucleotides to form duplex DNA will then result in the conjugation of the stimulus-responsive component to the protein near the engineered thiol attachment site. Since the register of duplex formation can be exactly specified by the sequences of the two oligonucleotides, the conjugation distance of the stimulus-responsive component to the thiol attachment site can be easily specified by the start site of duplex complementarity. This distance can be used to control the gating and switching activity of the stimulus-responsive component at the protein binding site or enzyme active site.

g. Target Ligands

The target ligands, as defined herein, refer to the molecule bound by the molecules defined above where the binding reaction can be modified or otherwise manipulated through the interaction of the stimulus-responsive component molecules bound to the molecules. These may be substrate, in the case where the molecule is an enzyme, ligand bound by a receptor, or a complementary nucleic acid. A specific site on the ligands, i.e., substrate, receptor ligand or complementary DNA, may also be conjugated to a responsive stimulus-responsive component, with sensitivity to the same or a different stimulus from that of the first stimulus-responsive component bound to a specific site on the protein.

3. Immobilization of the Molecules and/or Ligands on Solid Surfaces

In some embodiments, the target interactive molecule may be immobilized to a solid support. This can be any form of porous or shaped solids, particulates, chromatography medium, or other solid surfaces known to those skilled in the art. The molecules may be bound using commercially available reagents and standard techniques, usually through the formation of covalent bonds or affinity interactions between the support and the molecules.

Figure 5:
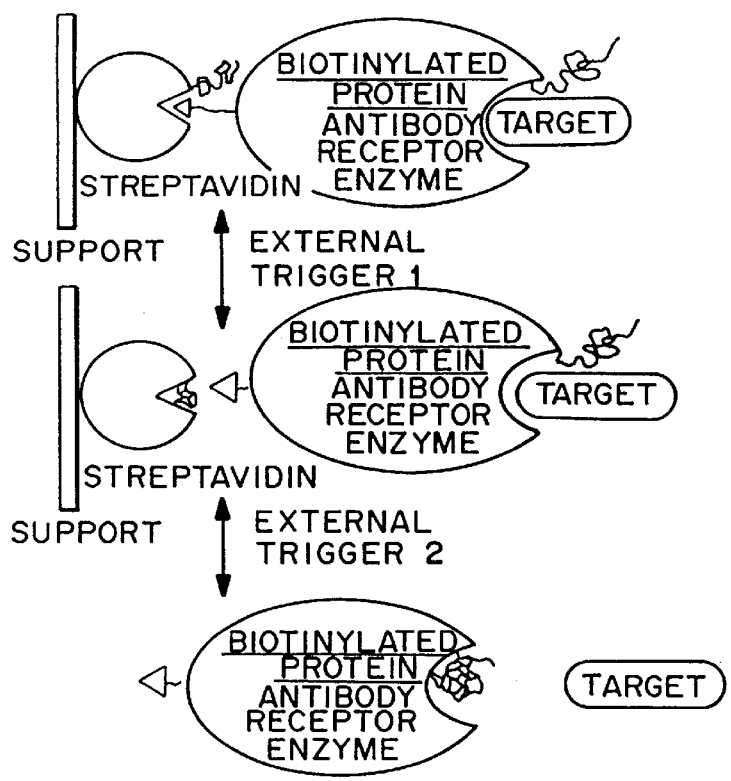
FIG. 5 is a schematic illustration of the use of a responsive-polymer/engineered-protein conjugate in a separations application. The support can be a conventional chromatographic resin, an HPLC support, a particulate or porous support such as a microporous membrane or hollow fiber, a bioreactor surface, or other means for immobilization. As depicted, the receptor is streptavidin having conjugated thereto a stimulus-responsive polymer and the ligand is a biotinylated protein such as a biotinylated antibody, or enzyme, which further includes a binding site for an analyte or other target molecule and a stimulus-responsive molecule which can block or allow binding upon exposure to a second, different stimulus. The same format can be used in aqueous two-phase separations, where the polymer-protein conjugates are reversibly partitioned in one or the other phase, or at the interface between them.
Figure 6:
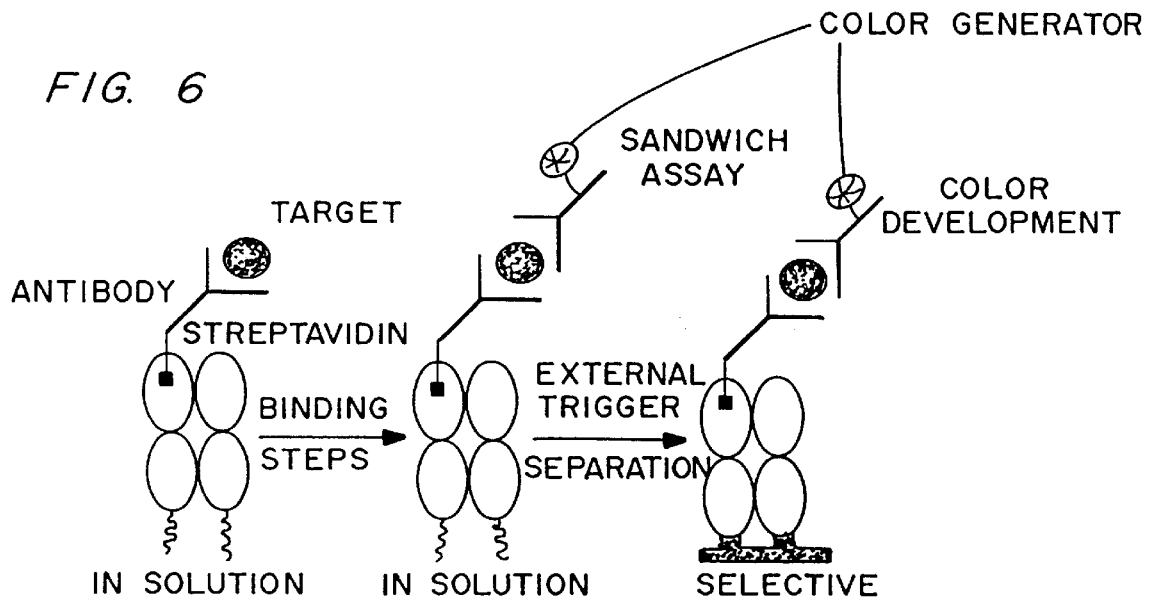
FIG. 6 illustrates an immunoasssay format using the stimulus-responsive polymer-interactive molecular conjugate compositions to complex the target analyte (ligand) and a second, labeled receptor in solution, which may be followed by phase separation to isolate the signal at a solid interface or in a separate liquid phase or liquid-liquid interface.

As shown in both FIGS. 5 and 6, the interactive conjugates are ideal for use in separations. As shown in FIG. 5, one stimulus-responsive molecule can be used to control binding to a support to separate out of a solution or mixture a protein such as a biotinylated protein that binds a target such as an analyte. The second binding site for the analyte can be further controlled through the use of a second stimulus-responsive molecule, which allows or blocks binding upon exposure to a stimulus. This provides a means for detecting a target molecule and purifying the molecule, then regenerating the starting materials so that they can be used again. FIG. 6 provides a variation of this method, where the target molecule is bound to an antibody linked to an indicator molecule, which if activated, serves as a signal to exposure the binding molecule, the streptavidin to a stimulus which collapses a stimulus-responsive molecule to allow binding and immobilization of the steptavidin-antibody-target conjugate to a substrate.

To immobilize the stimulus-responsive component/site specific protein conjugates to a stimulus-responsive component support, covalent bonding of protein lysine groups to an activated polymer support surface can be used. Reactive groups (e.g., —OH, —COOH, —NH$_2$) are needed on the surface of the polymeric support, such as a microporous membrane, microparticle, or a 96-well microtiter plate. The amine group is usually more reactive than the —OH or —COOH groups. There are several ways that amine groups can be formed on polymer surfaces;, as depicted in FIG. 9: (a) physical adsorption of polymers containing amine groups onto oxidized, ozonized or other negatively charged surfaces, where the polymer is bound mostly by ionic interactions, or onto hydrophobic surfaces where the polymer is bound mainly by hydrophobic interactions, (b) physico-chemical deposition of "polymers" containing amine groups from amino-monomer (e.g., allyl amine, heptyl amine, etc.) gas discharges; (c) chemical coupling of long chain alkyl amines onto hydrophobic substrates using an argon gas discharge; (d) chemical immobilization of amine polymer or their precursors by covalently-conjugating reactive polymer groups to reactive surface groups, or by physical adsorption of the polymer followed by treatment with ultraviolet radiation (uv), high energy radiation, or gas discharge; or (e) graft polymerization of amino-monomers (e.g., aminoethyl methacrylate) using ozone, gas discharge, high energy radiation, or UV to initiate the polymerization.

Vinyl formamide, which is a polymerizable monomer whose pendant formamide groups are readily hydrolysed to amine groups after polymerization, can be similarly surface graft polymerized. Acrylic or methacrylic acid, plus AAm or HEMA, can be graft copolymerized to form surfaces with varying contents of carboxyl or hydroxyl functionalities. The carboxylated surfaces may also be used to physically bind, by ion—ion interactions, polycations such as polyethylene imine (PEI) or poly vinyl amine. In addition to these surface modifications, reactive microparticles and microporous membranes can be purchased, e.g., from Bangs Laboratories, Sigma, Polysciences, Millipore, Pall, Gelman, Sigma, Cole-Parmer, Alltech, etc. For example, hydrophilic PVDF microporous membranes onto which various polyamines (or their precursors) were first physically absorbed have been treated in a "flow-through" gas plasma, by moving the plasma through the membrane pores of a fixed membrane to covalently immobilize the polyamine (or its precursor). (In some cases, the membranes can be purchased with reactive surface groups).

Although described with reference to modification of surfaces with amine groups, the processes for formation of carboxyl and hydroxyl groups on surfaces are parallel processes.

Activation of the reactive surface groups, followed by immobilization of the stimulus-responsive component/site-specific protein conjugate by covalent bonding of protein lysine groups to the activated polymer support surface, is accomplished using well established immobilization chemistry methods.

II. Methods of Use of the Interactive Molecular Conjugates

The uses of the stimulus-responsive component-directed affinity and partitioning switches for the interactive molecules are as numerous and diverse as the biotechnological, medical, laboratory, and industrial uses of the interactive molecules themselves. Thus, the stimulus-responsive component-interactive molecule conjugates are directly applicable to a wide variety of separations, sensors, diagnostics, bioprocesses, biointeractions, and drug delivery systems, and can also be applied to the design and application of new technologies, such as control of enzyme rate processes, stimuli-induced phase-separation immunoassays, regeneration/recycling of environmental sensors and biosensors, control of protein and cell interactions at foreign interfaces, and information storage, retrieval and signalling.

1. Affinity Switches

An embodiment of a solution-based affinity system, an "affinity switch," that is responsive to an external stimulus which triggers reversible binding and release of the target ligands, which specifically interacts with the interactive molecule of interest, is depicted in FIG. 1a, where a unique thiol functionality 10 is located near the binding pocket 12 of a ligand-binding protein 14 and sulfhydryl-specific polymer chains 16 (illustrated as a "snake-like" ribbon structure) are conjugated to the protein 14 to provide externally-triggered steric inhibition of the ligand binding equilibrium.

The release of the target ligand is controllable, and can occur in solution (typically accompanied by simultaneous precipitation of the stimulus-responsive component-affinity molecule conjugate after it has released the target molecule), or at a specific surface, phase, or interface, where it can be immobilized on the surface at the interface, or entrapped within a hydrogel, in a capsule, hollow fiber, or a pore of a porous solid.

Figure 2D:
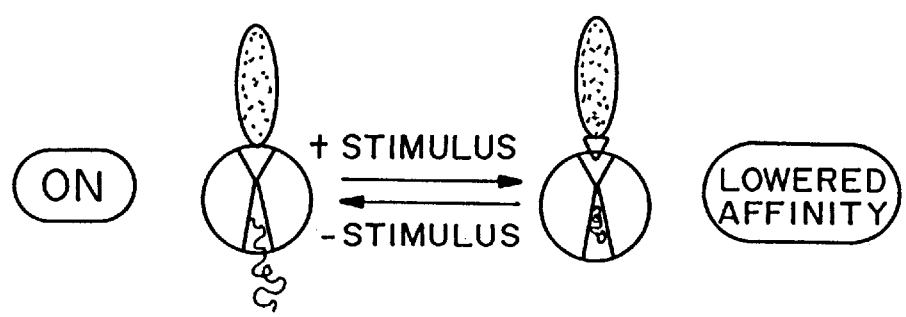

Four different embodiments of the affinity switch actions of the responsive polymer-interactive molecule conjugates are depicted in FIGS. 2a–d. Stimulation of the polymer may cause the ejection of bound ligand (FIG. 2a) or steric blocking or unblocking of the binding pocket (FIG. 2b), or it may cause a ligand tethered to another site on the protein surface to be withdrawn from the binding pocket (FIG. 2c), or the allosteric modification of the affinity binding equilibrium within the binding pocket (FIG. 2d). In order to enhance any of these actions of the conjugated polymer, it is also possible to conjugate more than one polymer to different, specific sites on the protein surface, or to combine a site-specific conjugation of one polymer with non-specific conjugation of other polymer chains to the same protein. FIG. 2c shows an embodiment where a stimulus-sensitive polymer (e.g. light sensitive ligand dye) is stimulated (e.g. with light) to cause a conformational change which reduces its affinity for the ligand binding pocket, while the polymer chain conjugated to the interactive molecule is stimulated by a different stimulus such as temperature, causing it to contract or phase separate, the combination of these actions causing the lowered affinity ligand dye to be "pulled" from the pocket. Either stimulus can be applied first, or the two may be applied simultaneously. The combined action can result in the exposure of the open binding pocket for subsequent affinity binding by the ligand. Reversal of the stimulus should permit reverse behavior.

Figure 14:
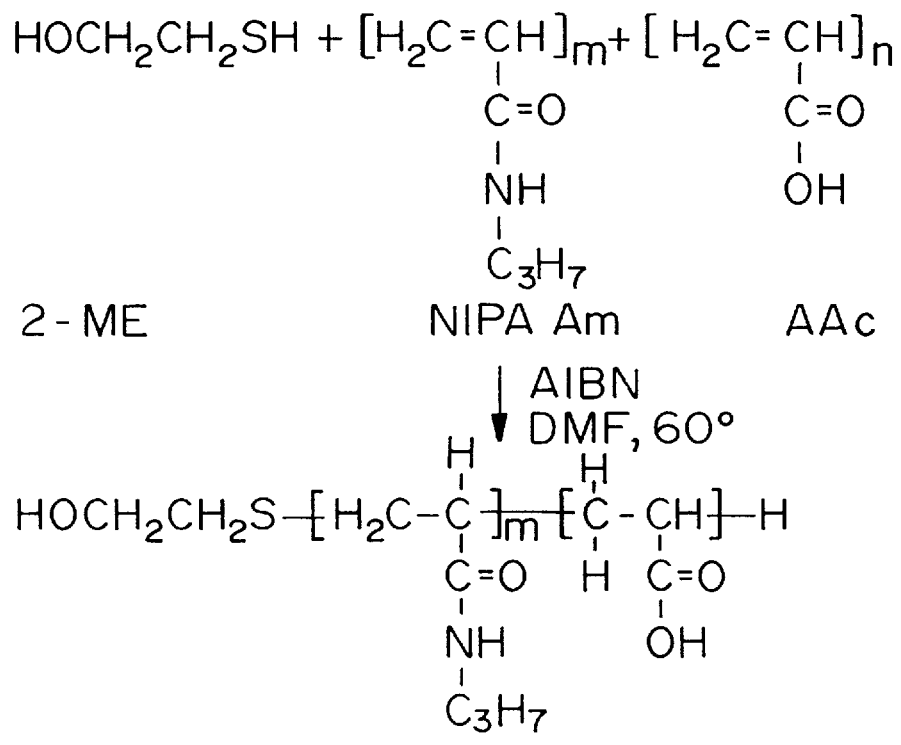
FIG. 14 illustrates the synthesis of poly(NIPAAm/AAc) with a terminal hydroxyl group by chain transfer free radical copolymerization

The optimum site within the pocket for each specific composition and molecular weight of polymer for ejection of the ligand (e.g. biotin derivative in the case of streptavidin, for example) when the polymer is collapsed by raising the temperature, or expanded by lowering the temperature, is determined initially by utilizing different molecular weight polymers such as PNIPAAm polymers of different molecular weight (FIG. 14). More (or less) hydrophilic copolymer compositions are then employed. These variables will influence the degree of conformational change of the polymer chain with temperature.

In the case of the tethered ligand approach (FIG. 2c), bifunctional responsive polymers of different molecular weights, can be used to determine the optimum site for "uncorking" the ligand out of the binding site when the polymer is collapsed, for example, by raising the temperature. The "uncorking" may be tested with or without the light stimulus that affects the dye ligand binding affinity in the binding site (see also FIG. 4). Similar strategies can be applied to protein G and monoclonal antibody.

The affinity switch is particularly useful where the stimulus-responsive component is used to displace material which has bound to and fouled the affinity site as in the case of affinity-based environmental sensors, biosensors or separations systems. Similar considerations apply to the fouling of enzyme active sites in bioprocesses, as well as in the above application areas. Free protein binding sites, such as the antigen binding sites of antibodies or the active sites of enzymes, need to be regenerated for use in sensor, separation and enzyme technologies. For example, an antibody recognizing an environmental toxin might be immmobilized on the surface of an optical sensor, where the binding of the target toxin leads to an optical signal that is transported to a detector. For the sensor to be used again, the target toxin must be removed from the antibody binding site, without damaging the antibody or the optical sensor. In one embodiment, the stimulus-responsive polymer-antibody conjugate can be immobilized on the optical sensor, and after the initial binding and detection step, the target toxin can be removed without the need for harsh elution conditions by stimulating the polymer to switch the toxin out of the binding pocket. There is also a need to remove bound products from the active sites of immobilized enzymes, which inhibit bioreactor catalysis through product inhibition. In a second embodiment, the stimulus-responsive polymer-enzyme conjugate can be immobilized in the bioreactor, and when product inhibition becomes a problem, the enzyme active site can be regenerated by stimulating the polymer to switch the product out of the active site. In a third embodiment, a prodrug may be activated by enzyme-induced release of an active drug, such that reactivation of a fouled enzyme active site can lead to renewal of drug delivery. In some cases, the prodrug or a polymeric prodrug may be conjugated randomly or specifically to the enzyme, such that when the enzyme active site is regenerated by a stimulus it causes a burst of drug release. The "cork-pulling" action depicted in FIG. 2c may also be used to regenerate enzyme activity upon stimulating the polymer and the ligand bound is the active site, as described above.

The binding affinities and/or the binding kinetics of the target ligands with the stimuli-responsive polymer-engineered protein conjugates are measured as a function of temperature change, pH change, or intensity, time and wavelength of light (UV or visible) exposure. Binding assays include ELISA assays, radiolabel-based assays (e.g. equilibrium dialysis), and optical absorbance/ fluorescence-based assays. A well-established assay for determining the off-rate of radiolabeled biotin is described in co-pending patent application U.S. Ser. No. 08/387,055, and thus increased off-rates with the stimulus-responsive polymer-streptavidin conjugate can be directly measured.

2. Partition-Switches

The stimuli-responsive stimulus-responsive components can also provide a trigger for selectively precipitating or partitioning a polymer-protein conjugate, in the latter case to a liquid-liquid interface, into a second aqueous phase, or onto selected polymer surfaces, as generally depicted in FIGS. 3a, b and c. The stimulus-responsive component may be conjugated to specific sites away from the interactive molecule's ligand recognition site, so that the precipitation only causes phase separation, referred to herein as "partition-switching", and not "affinity-switching". After the externally-triggered precipitation of the individual polymer chains occurs, the conjugates can aggregate together and precipitate out of solution, as generally described for random conjugation of PNIPAAm to affinity proteins such as in the case of a PNIPPAm-antibody/antigen/second antibody conjugate/complex molecule precipitating out of solution, by Monji and Hoffman, *Appl. Biochem. Biotechnol.* 14:107–120 (1987) and also in the case of a PNIPPAm-protein A-IgG conjugate/complex molecule precipitating out of solution, by Chen and Hoffman, *Biomaterials* 11:631–634 (1990)). Site-specific conjugation of the polymer to the recognition protein as described herein should lead to greater retention of the recognition capacity of the protein than random conjugation, e.g., to lysine amino groups, on the protein.

In the presence of a selected polymer surface, the precipitating polymer chains may selectively bind to specific surfaces. Phase partitioning of the polymer-protein and polymer-molecular conjugates to a second aqueous phase can also be directed by the precipitated polymer (Diamond and Hsu, *Adv. Biochem. Eng. Biotechnol.* 47:89–135 (1992); Walter et al., *Anal. Biochem.* 197:1–18 (1991); Hoffman, *J. Biomat. Sci Polymer Ed.,* 5:555–568 (1994).

These approaches offer at least two important advantages over conventional methodologies: rapid reversibility of protein recognition processes and/or protein separation processes using an environmental signal, and greatly reduced non-specific binding of interactive molecules to conventional support surfaces.

3. Combination Partition and Affinity Switches a. Using Two or More Stimuli-Responsive Stimulus-responsive components with Different Functions The affinity trigger and partition trigger capabilities can also be combined with the same interactive molecule such that two different stimulus-responsive components are conjugated at two different locations. Partitioning is triggered by a different external signal than that which triggers the ligand blocking/unblocking or binding/release actions. With dual triggering capabilities, for example, as shown in FIG. 4 a interactive molecule-stimulus-responsive component conjugate, with its target ligand bound, can first be phase-separated by triggering the stimulus-responsive component conjugated away from the binding site, followed by the use of a second signal which triggers the affinity switch and releases the ligand, in a desired phase or at a desired surface. This can be accomplished by attaching one class of stimulus-responsive component near the ligand binding pocket, for example, a light-sensitive polymer, and a separate polymer chain at the partition triggering site, for example, a temperature sensitive polymer. Alternatively, two stimulus-responsive components within the same class, but with distinctly different stimuli-responsive conformational changes (e.g., having two different phase separation temperatures), can be used.

b. Using Mixed-function Conjugates

The ability to generate streptavidin tetramers from non-identical monomer subunits permits unique uses of the polymer-protein conjugates which require mixed functional properties. For example, two of the subunits can be individually engineered with cysteine attachment sites near the binding site. These sites can then be conjugated with, e.g., temperature-responsive polymers, thereby providing a temperature-controlled affinity switch. The remaining two subunits can be individually engineered to contain engineered cysteine residues located away from the binding site, for the conjugation of different stimulus-responsive components, e.g., pH-sensitive polymers directing selective pH-responsiveness, such as precipitation, or providing a pH-sensitive partitioning switch. The mixed-function polymer-streptavidin conjugates thus combine a temperature-sensitive ligand affinity binding switch with a pH-sensitive selective partitioning trigger. Similar mixed dual response conjugates can be made from two different temperature-sensitive polymers that have different cloud point temperatures (see FIGS. 5 and 6). The polymers themselves may also be composed of both temperature and pH components, or other combinations of different sensitivity components.

c. Rate- or Affinity- Controlling Switches

As discussed above, the size and conformation of the stimulus-responsive component can be used not only to block binding, i.e., turn binding "on" or "off", but also to regulate the rate and extent (or affinity) of binding as well as to selectively permit only ligands below a certain size to have access to the binding site. Once the size of the binding or active site and the affinity ligand or enzyme has been determined, one can select the molecular weight, composition and structure of the polymer, which will define the stimulus-induced conformational changes of the stimulus-responsive component to determine the extent to which the site is blocked. It is routine to optimize the extent of blocking which is desired, for example, by conjugating a series of stimulus-responsive components of different molecular weights or compositions to the interactive molecule and measuring binding before and after exposure to a stimulus which alters the conformation of the stimulus-responsive component.

The influence of polymer composition, molecular weight and structure, and the type and magnitude of the stimulus applied to the polymer can be determined for each target ligand or cell to the immobilized stimulus-responsive component/site-specific protein conjugates. The stimulus-responsive component properties and the site-specific cysteine location(s) for the most controllable and reproducible "on-off" responses of each of the three affinity recognition proteins can thereby be optimized for each ligand.

4. Specific Applications

Due to the ability to control the affinity interaction between the interactive molecule and target ligand, many uses of the conjugates described herein are found in separations, diagnostics, sensors such as environmental sensors and biosensors, drug delivery, bioreactors and immobilized enzyme technologies, biocompatibility, etc. For example, in the case of an enzyme, stimulus-responsive, "on-off" or modulated control of enzyme activity can be achieved, (e.g. control of turnover rate and substrate size-specificity), a feature that has important uses in bioreactors, sensors such as biosensors and environmental sensors, separations and drug delivery.

a. Separations Applications

In separations applications, the stimulus-responsive component/site specific interactive molecule conjugates are useful in, e.g., low pressure chromatography, high performance liquid chromatography, affinity precipitation separations, membrane separations, immunoadsorption separations, and two phase aqueous separation systems. Site-specific binding molecules such as streptavidin, protein G, and monoclonal antibodies, exemplified herein, are the most widely-used affinity proteins in current affinity separations systems. The widespread uses of streptavidin, antibodies, and protein G are discussed in Wilchek, 1990, supra; Harboe et al., *J. Clin. Microbiol.* 28:913–921 (1990); Katz and Siewierski, *J. Chromatogr.* 624:403–409 (1992); Meyer et al., *Exp. Hematol.* 19:710–713 (1991); Paganelli et al., *Int. J. Cancer* 45:1184–1189 (1990); and Yarmush et al. *Biotechnol. Prog.* 8:168–178 (1992). Because streptavidin and a biotinylated antibody, protein G, and IgG are often used together, the conjugation of a stimulus-responsive component to one or both of them provides the opportunity to sequentially (and temporally) regulate the affinity of each component. Each protein can be modified with a stimulus-responsive component to respond to a different or unique stimulus, allowing specific interfaces and molecular interactions to be switched on or off by the choice of stimulus.

A representative dual affinity trigger separations application is illustrated schematically in FIG. 5. As shown in FIG. 5, one stimulus-responsive molecule can be used to control binding to a support to separate out of a solution or mixture a protein such as a biotinylated protein that binds a target such as an analyte. The second binding site for the analyte can be further controlled through the use of a second stimulus-responsive molecule, which allows or blocks binding upon exposure to a stimulus. This provides a means for detecting a target molecule and purifying the molecule, then regenerating the starting materials so that they can be used again.

For example, the streptavidin-biotinylated antibody interaction can be controlled with temperature, while the antibody-target antigen interaction can controlled by pH. Two different temperature-responsive polymers can also be used, where, for example, the external temperature is raised to affect the release of the biotinylated antibody-target ligand from streptavidin first, and then the target molecule is separated from the antibody by raising the temperature a few more degrees. While a solid support for the reaction can be used, e.g., using a conventional chromatographic resin, an HPLC support, membrane, bioreactor surface, etc., the affinity switches can also be applied to precipitation or two phase, aqueous separation strategies. The physical properties of the partially or totally collapsed polymer, which is usually hydrophobic, differ significantly from the extended coil, which is usually hydrated and hydrophilic, providing the driving force for reversible partitioning between two aqueous phases.

In another example, an optimized stimulus-responsive component-engineered protein conjugate system is designed for selective separation of lymphocytes or other cells carrying biotinylated monoclonal antibodies bound to cell receptor proteins or carbohydrates.

Stimulus-responsive component/site-specific protein (streptavidin) conjugates are immobilized onto BIO-RAD acrylamide-acrylic acid gel beads which are currently used for selective lymphocyte cell separation protocols. The beads have carboxyl functionalities, and avidin is immobilized to the beads using conventional carbodiimide activation protocols. The cell selections are carried out with bone marrow or peripheral blood, or model system preparations using a biotinylated CD34 antibody, which binds to stem cell CD34 membrane receptors which are present in the cells that are to be positively selected. The cells which are selected by binding to the column are removed by gentle squeezing of the flexible column followed by eluting the separated cells from the column. Since the cells break off the column and leave behind the biotinylated CD34 antibody, which is still bound to the immobilized streptavidin conjugate, the stimulus-responsive component/ streptavidin conjugate is stimulated to eject the biotinylated antibody to be able to reuse the column. The ability to reuse the column is useful for separation applications other than bone marrow separations.

Separation of Antibodies using an Immobilized Stimulus-Responsive Component-Protein G Conjugate.

In still another example, the optimized stimulus-responsive component/site-specific protein conjugate system is used for separation of antibodies with an immobilized stimulus-responsive component-protein G conjugate. A biotinylated stimulus-responsive component/ protein G derivative (biotinylated via amino groups from lysine side-chains) is immobilized in streptavidin-coated microtiter wells, using streptavidin-conjugated SEPHAROSE" as a stationary support. The stimulus-responsive component-protein G conjugate can be covalently immobilized on commercially available SEPHAROSE" beads through the amino groups of lysine side-chains. This system is then applied to separation of IgG antibodies. A solution containing IgG (e.g., whole blood, blood plasma, blood serum or a bioprocess product stream) is reacted with the SEPHAROSE affinity beads and IgG binds to the Protein G. The antibodies are first bound under environmental conditions where the stimulus-responsive component is in a physical state where binding is allowed. The beads are rinsed and the IgG molecules are released with the appropriate temperature, pH, light or other stimulus switch. Conditions are determined for sequential binding and release using a pure antibody preparation, and mixtures of antibodies and other proteins, including whole blood, blood plasma, and whole cell extracts containing antibodies. The initial runs are conducted as a function of ionic strength to minimize non-specific interactions. In the case of separation of IgGs from whole blood or plasma, the IgGs may first be concentrated from whole blood by cryoprecipitation, then rewarmed to redissolve, and affinity-purified on the Protein G column as described; this will avoid the need to handle large volumes of blood or blood plasma in the Protein G column.

Selective Separation of Specific Antigen Carrying Cells.

The immobilized stimulus-responsive polymer-scFv antibody site-specific conjugate system is also used for selective separation of specific antigen-carrying cells, such as CD44 cells. The same immobilization approach as that described above is used to cross-link the stimulus-responsive polymer-scFv antibody conjugate to Bio-Rad acrylamide-acrylic acid gel beads. As the S5 scFv antibody can be biotinylated through lysine groups without altering the binding affinity, avidin-coated beads can be used as well to immobilize the scFv conjugate. The affinity switch can, for example, then be used to isolate human peripheral blood mononuclear cells (PBMC) which express the CD44 antigen, starting with pure PBMC cells and proceeding to more complex mixtures, as well as cells that express lower quantities of CD44 which can be discriminated against.

General Advantages for Separations

There are many significant advantages of such stimulus-responsive component/site specific protein conjugates in separations, such as: 1) gradual or rapid and quantitative elution of the bound target ligand, provided by the stimulus-responsive component which is conjugated near the protein active-site; 2) external stimuli used to trigger stimulus-responsive component precipitation and conjugate phase partitioning are mild compared to currently required elution conditions, and are thus more likely to preserve the integrity of target molecules; 3) gradual or rapid reversibility between on and off binding states, which provides more versatile and cost-effective separation systems; 4) the opposing factors of selectivity and separation efficiency can be optimized by moving the stimulus-responsive component conjugation site closer to or further away from the binding site or active site of the protein or enzyme, as desired and also the composition of the polymer may be modified to control its conformation as a function of the level of the stimulus, such that only certain size ligands may bind during exposure to a complex mixture, e.g., by raising the temperature to partially collapse the polymer chain and block the binding of large ligands, but still remaining below the temperature where the polymer is completely collapsed, followed by raising the temperature higher to eject and recover or discard the small bound ligand; 5) the stimulus-responsive component can act to stabilize the affinity protein in solution or on a surface, thereby providing a longer operating time and greater economic advantage for the separation process; 6) in the case of the stimulus-responsive component-streptavidin conjugate with biotin as the target ligand, the biotin may be conjugated to a wide variety of interactive molecules, such as antibodies, drug molecules, enzymes, peptide ligands, and cell receptors, all of which permit a myriad of potential applications for the stimulus-responsive component/site specific protein conjugate system, 7) the stimulus-responsive component composition and molecular weight can be adjusted and matched to each conjugation site to optimize the desired response (e.g. type, magnitude, rate, for example, where a collapsing polymer is used to selectively separate small and large ligands with the same affinity ligand constructs). Other advantages include the ability to block ligand access to the binding site until the stimulus is revered, expanding and hydrating the polymer coil.

b. Diagnostic Applications

In vitro diagnostic methods can be designed which employ stimulus-responsive component/engineered protein conjugates. For example, in one embodiment, depicted in FIG. 6, illustrating an immunoassay format using the stimuli-responsive polymer-interactive molecule conjugate compositions, the protein is streptavidin and is used in conjunction with a biotinylated monoclonal antibody. An exemplary assay begins with a homogeneous, solution-phase incubation of the biotinylated monoclonal antibody with the analyte solution, which contains the antigen plus an added, labeled monoclonal antibody to a different epitope on the antigen, forming the immune complex sandwich. This is followed by addition of the stimulus-responsive polymer/ streptavidin conjugate, which will bind the biotin conjugate, after which the polymer is stimulated to affect a physical separation to isolate the analyte and the signal antibody complexed to it. This homogeneous incubation/phase separation technique offers significant advantages over conventional solid-phase ELISA technology, which include: 1) ability to complex large analytes in a homogeneous incubation step; 2) greatly reduced background signal caused by non-specific binding of the labeled monoclonal antibody on solid surfaces binding with solution phase binding steps; 3) avoidance of the partial loss of Ab recognition sites arising from its physical adsorption in an unfavorable orientation on solid surfaces, as in ELISA; and, 4) reduced processing requirements, including significantly reduced washing requirements, along with speedier acquisition of results. These diagnostic protocols can be used with a monoclonal antibody, and therefore, any specific antigen target. They also provide rapid and efficient optimum monoclonal antibody/ antigen binding, because the recognition step occurs in solution. The processing of test results also has significant advantages over traditional methods, with controlled rate or fast response to external signals such as light or temperature, and ability to test multiple samples using colorimetric-based assays (e.g., using microtiter well surfaces to collect, by triggering the phase separation onto the surface, the polymer-streptavidin/biotin-monoclonal antibody/antigen/secondary labeled MAb conjugate/ complexes.

In another application of this technology, when the polymer is in the collapsed state, the sensor action is turned off since the analyte ligand cannot bind to the recognition protein. This "off" state also serves to protect the protein's active site from fouling by various agents in the environment. In this case, it may be desirable to be able to turn "on" an environmental sensor only at specific times, in order to sample the concentration of a particular analyte in the environment at those times, while retaining the sensor protein in a protected state the rest of the time. In addition, there are disposable sensor packets that operate by flow of a test solution containing multiple analytes through various sensing channels containing different sensing elements. In this case, it may be desirable to turn "on" the sensor protein only when the test solution has reached and become distributed within the recognition protein channel in the most efficient manner. In both of these examples, after the sensing is completed, the action of the recognition protein is regenerated by reversing the stimulus (e.g., heating) to remove the analyte from the active site, and to keep it in the "off" state thereafter until needed once again.

c. Drug Delivery Applications

The stimulus-responsive component-protein conjugates described herein provide a significant means for combining drug targeting capabilities or in vivo diagnostic methods with triggered delivery. Streptavidin has been used in targeted drug delivery systems by first conjugating it to a targeting moiety such as a carbohydrate ligand for a cell membrane receptor or an antibody and injecting it to deliver it to a specific cell, and then injecting and binding to it biotinylated imaging or therapeutic agents such as radioisotopes or anti cancer drugs. Bickel, 1993; Pardridge, 1992; Sheldon, 1992; and Paganelli et al., *Int. J. Cancer* 45:1184–1189 (1990), each of which is incorporated by reference herein. Alternatively, two and three step pretargeting methods can provide benefits of higher specificity and faster clearance of more toxic therapeutics or imaging agents, where the biotinylated carbohydrate or antibody is first administered, followed by injection of a streptavidin-biotinylated therapeutic complex (two-step), or followed by streptavidin and after that subsequently with the biotinylated therapeutic (three-step) (Paganelli et al., supra.).

Streptavidin's usefulness arises from its multiple binding sites (as well as its high affinity for biotin), so that one binding site can be used to target the protein and other sites can be used to complex biotinylated therapeutics or imaging agents. In the case of stimulus-responsive component-streptavidin conjugates, a biotinylated drug can be complexed in a streptavidin binding site which is complexed to the streptavidin-monoclonal antibody (SA-MAb) conjugate, and its release can be triggered later with a stimulus to collapse the polymer and eject the biotinylated drug.

Figure 7:
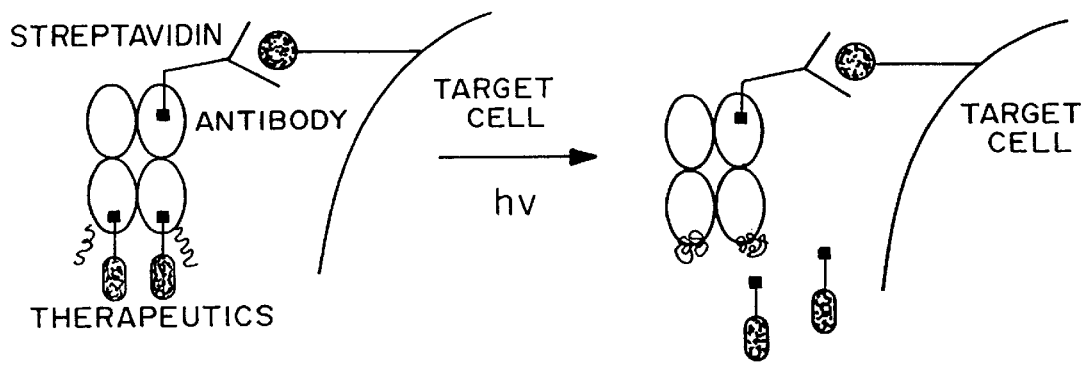
FIG. 7 illustrates an embodiment of the conjugated interactive molecule for the targeted delivery of drugs from a streptavidin delivery protein which is complexed both by a biotinylated-monoclonal antibody and by a biotinylated-drug. The biotinylated-drug binding sites are also conjugated with stimulus-responsive polymer, so that when the polymer is triggered by an external stimulus (e.g., a light pulse) the biotinylated drug is ejected from the binding pocket and delivered to the target cell. The two polymers may be triggered by the same or by different stimuli.
Figure 8:
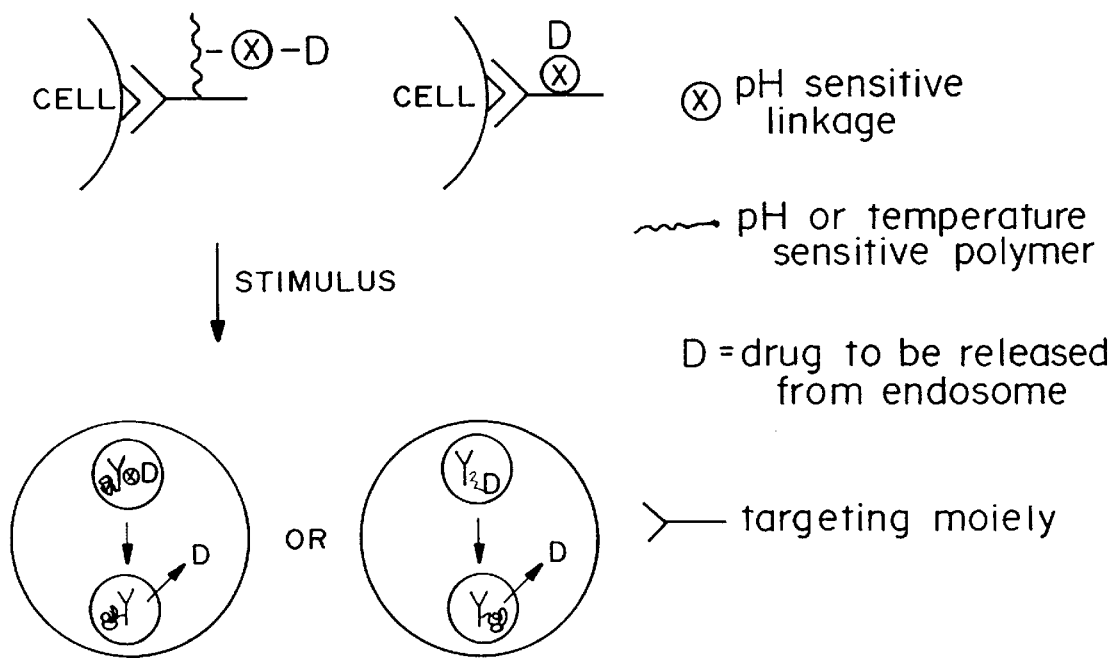
FIG. 8 is a schematic of delivery of a stimulus-responsive polymer-interactive molecular conjugate to a cell where drug is release by pH dependent cleavage of a linker to a drug.

A light-triggered affinity switch is particularly useful in drug delivery applications, where release of therapeutics after targeting is stimulated by collapsing the polymer, as depicted in FIG. 7. This method is especially useful for topical delivery, ophthalmic drug delivery, and internal delivery using catheters instrumented with a laser light source and optical fibers, to stimulate site-specific release. The collapse of the polymer chain can also be accomplished while its conjugate is complexed to a cell membrane receptor, which could stimulate receptor-mediated endocytosis. In such a case, the delivery of the drug can be triggered directly into the cell, within an endosome, for example, by triggering a polymer-antibody-drug conjugate (polymer-immunoconjugate). In this embodiment the antibody is engineered to provide a reactive —SH site for the polymer away from the binding site of the monoclonal antibody. The drug can be randomly conjugated to the monoclonal antibody or it can be conjugated to the polymer. The drug will be released inside of the endosome, for example, where the linkage of the polymer to drug is labile to a pH of approximately 4 or 5, the pH of the endosome, as shown in FIG. 8. FIG. 8 shows schematically the delivery of a stimulus-responsive polymer-interactive molecular conjugate to a cell where drug release is by pH dependent cleavage of a linker to the drug.

Enzyme-mediated drug delivery occurs by enzymolysis of prodrugs (i.e., inactive drug precursors, such as esterified acidic drugs). This approach is being utilized by pharmaceutical companies for enhancing drug penetration across cell barriers, such as in mucosal delivery systems. If a prodrug is synthesized by conjugating the drug to an enzyme inhibitor via an enzymolyzable bond, then complexation of that prodrug-inhibitor conjugate to the enzyme will block its enzymolysis. If a stimuli-responsive polymer is specifically conjugated near the active site of the enzyme, then triggering the polymer to eject the inhibitor will trigger the enzymolysis of the prodrug and release of active drug. The prodrug may also be synthesized by conjugating it via enzymolysable bonds as pendant groups along a polymer backbone, with the enzyme inhibitor also being conjugated separately to the polymer. Then when the prodrug polymer-inhibitor is ejected from the active site by the stimulation of the polymer conjugated to the enzyme nearby its active site, many drug molecules will be released by enzymolysis. The enzyme or enzyme-prodrug complex may also be targeted to specific sites, e.g., using biotin-streptavidin complexation as described above.

Figure 9A:
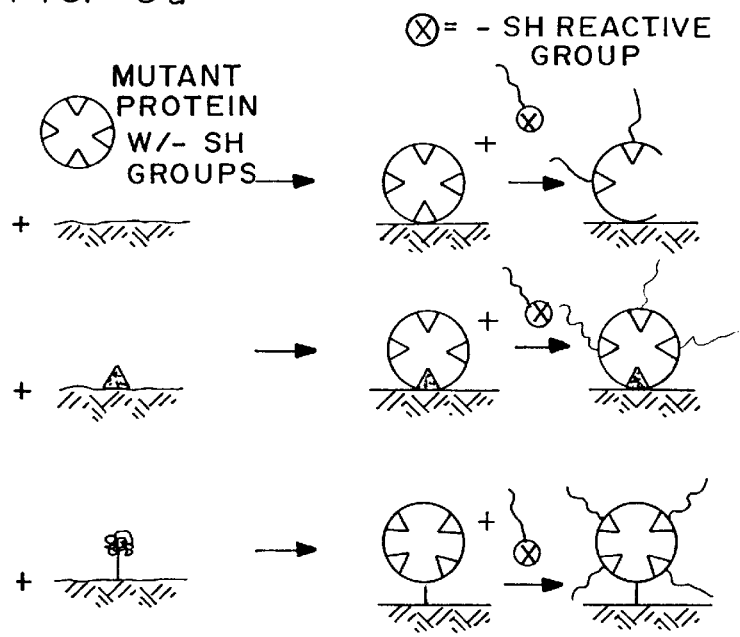
FIGS. 9a–c are schematics of three general methods for physical or chemical immobilization of a stimulus-responsive polymer-interactive molecular conjugate to a surface. In the first of the three general methods, (a) the interactive molecule may first be immobilized by non-specific adsorption (e.g., ionic, hydrophobic, etc.) or by affinity binding to surface ligand groups, or by chemically-coupling it to reactive surface groups, followed later by chemical conjugation of the responsive polymer to the surface-immobilized interactive molecule , or (b) the responsive polymer is first chemically-conjugated to the interactive molecule and then the conjugate is immobilized onto the surface by non-specific adsorption, or by affinity binding to surface ligand groups, or by chemically-coupling it to reactive surface groups, or (c) by first physically-adsorbing the responsive polymer onto the surface, or chemically-coupling the responsive polymer to reactive surface groups, followed by chemical conjugation of the interactive molecule to the surface-immobilized responsive polymer.
Figure 9B:
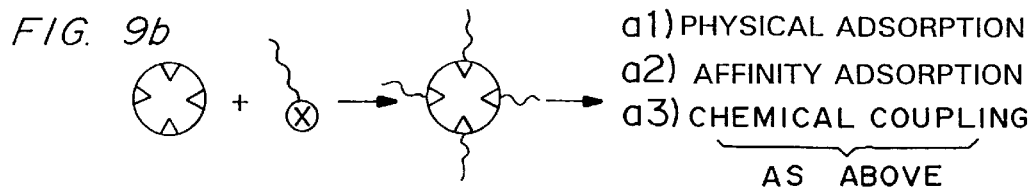
Figure 9C:
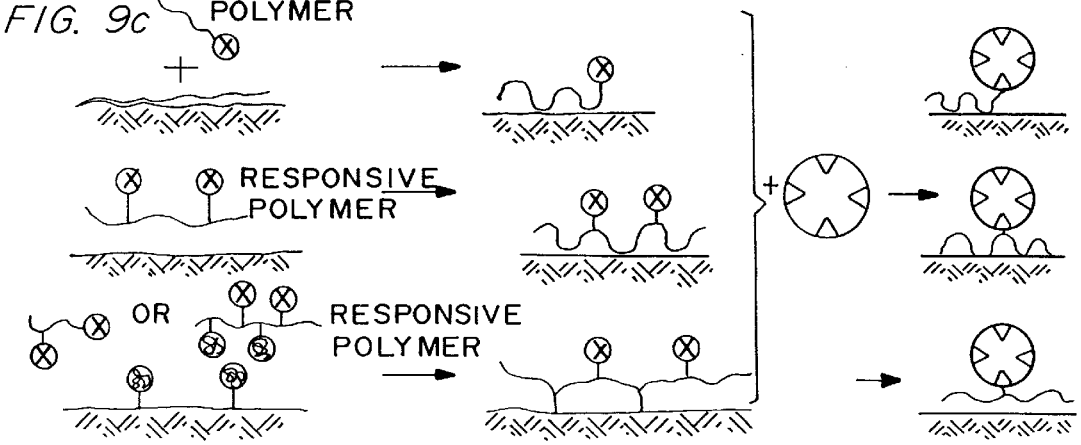

FIGS. 9a–c are schematics of three general methods for physical or chemical immobilization of a stimulus-responsive polymer-interactive molecular conjugate to a surface. In the first of the three general methods, (a) the interactive molecule may first be immobilized by non-specific adsorption (e.g., ionic, hydrophobic, etc.) or by affinity binding to surface ligand groups, or by chemically-coupling it to reactive surface groups, followed later by chemical conjugation of the responsive polymer to the surface-immobilized interactive molecule, or (b) the responsive polymer is first chemically-conjugated to the interactive molecule and then the conjugate is immobilized onto the surface by non-specific adsorption, or by affinity binding to surface ligand groups, or by chemically-coupling it to reactive surface groups, or (c) by first physically-adsorbing the responsive polymer onto the surface, or chemically-coupling the responsive polymer to reactive surface groups, followed by chemical conjugation of the interactive molecule to the surface-immobilized responsive polymer.

Figure 11A:
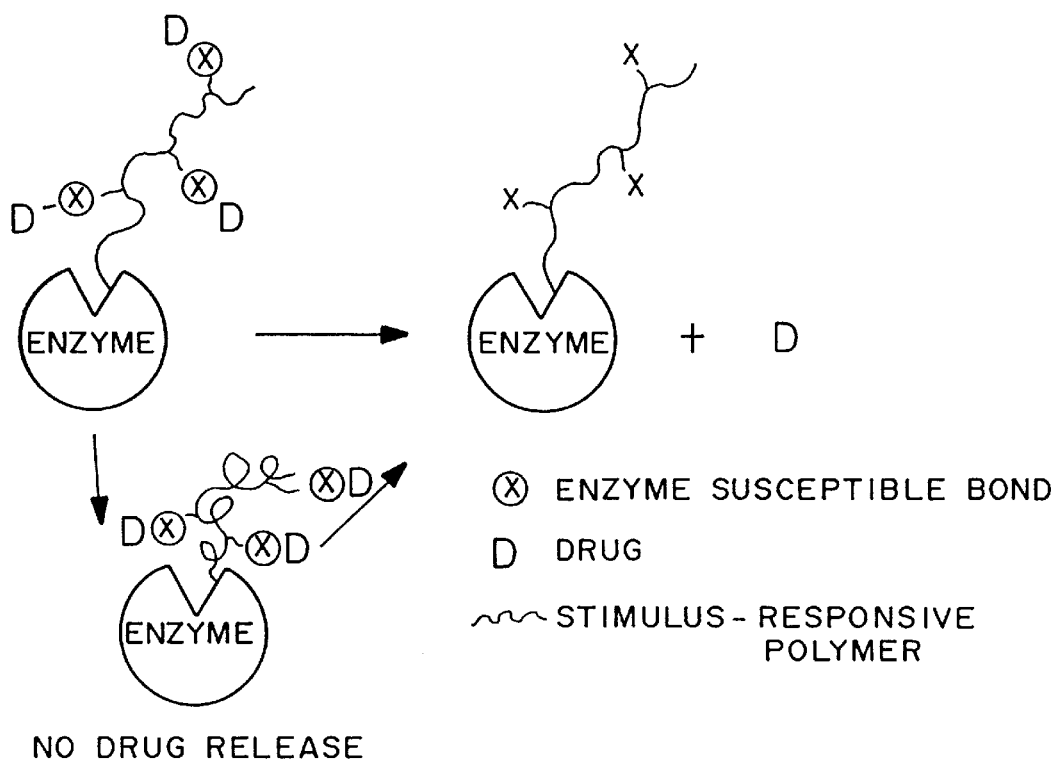
FIGS. 11a–c show the conjugate of a responsive copolymer and an enzyme, where the responsive copolymer has pendant drug molecules conjugated to the copolymer chain backbone by linkages that are degradable by the same enzyme to which the copolymer is conjugated. When the polymer is stimulated to collapse its coil, the enzyme is turned off, and it cannot release the drug by enzymolysis of the pendant linkages; when the reverse stimulus is applied, the enzyme becomes active and releases drug molecules by enzymolysis of the pendant linkages. A hydrogel, with an enzyme entrapped within the gel is shown in FIG. 11d.
Figure 11B:
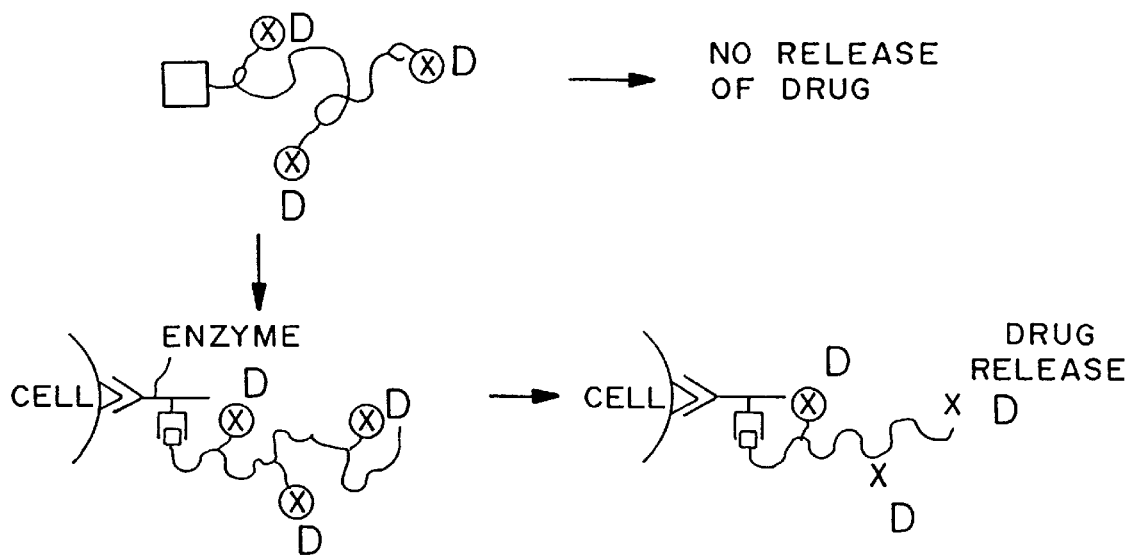
Figure 11C:
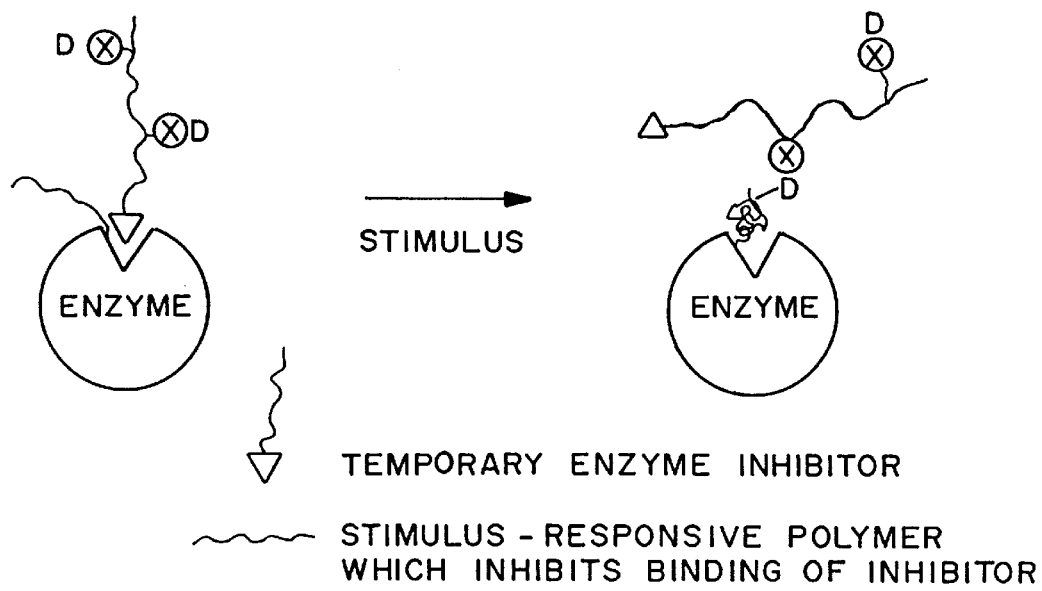
Figure 11D:
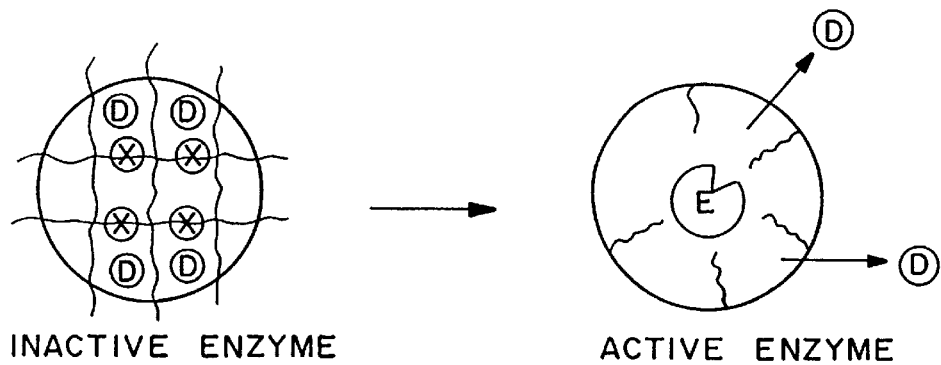
Figure 11D:
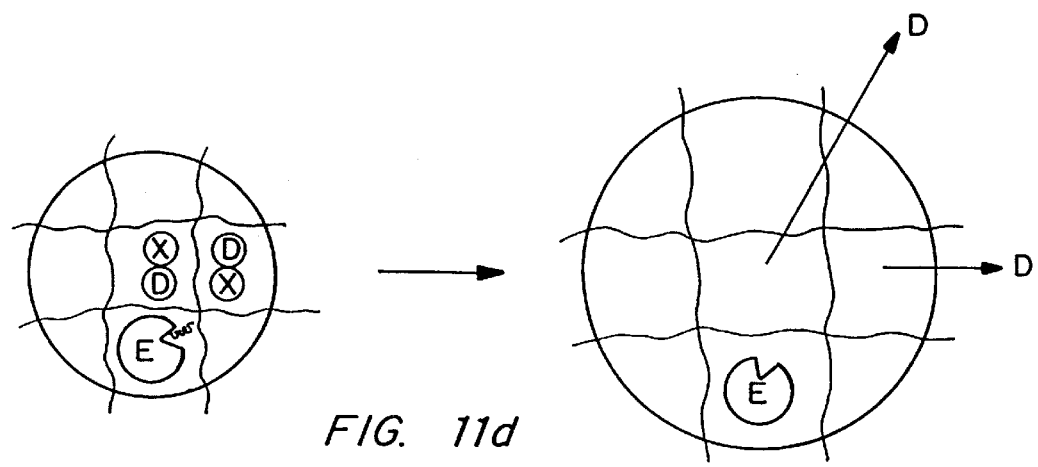
Figure 12A:
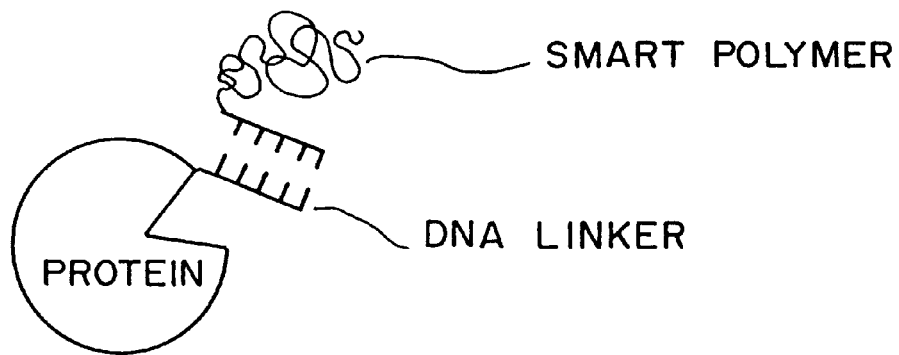
FIGS. 12a and 12b are illustrations of ssDNA hooks for "conjugating" the responsive polymers to the protein.
Figure 12B:
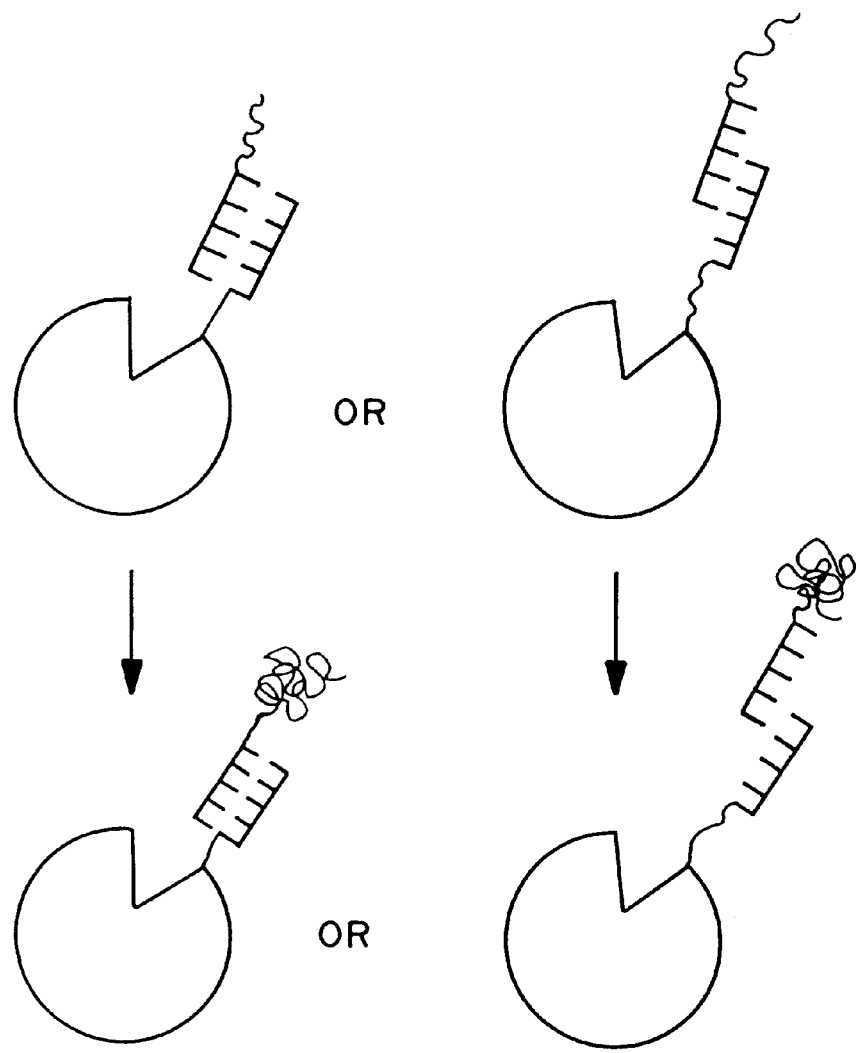

FIG. 11a–c show the conjugate of a responsive copolymer and an enzyme, where the responsive copolymer has pendant drug molecules conjugated to the copolymer chain backbone by linkages that are degradable by the same enzyme to which the copolymer is conjugated. When the polymer is stimulated to collapse its coil, the enzyme is turned off, and it cannot release the drug by enzymolysis of the pendant linkages; when the reverse stimulus is applied, the enzyme becomes active and releases drug molecules by enzymolysis of the pendant linkages. A hydrogel, with an enzyme entrapped within the gel is shown in FIG. 11d. FIGS. 12a and 12b are illustrations of ssDNA hooks for "conjugating" the responsive polymers to the protein.

Figure 16:
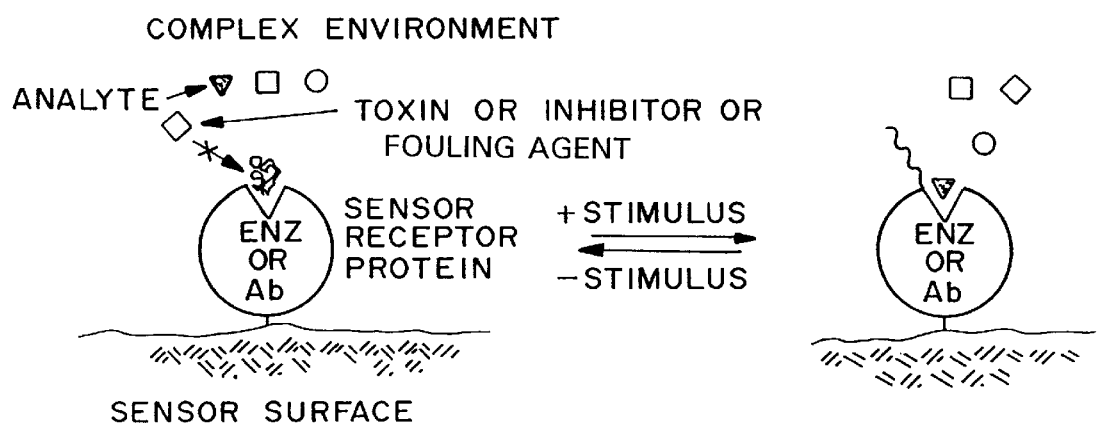
FIG. 16 is a schematic illustration of the use of a conjugate of a stimulus-interactive molecule and an interactive molecule such as an enzyme, antibody, or receptor protein as an environmental sensor. The sensor protein is protected and inactive until exposed to a stimulus. The interactive molecule binds to a molecule such as an analyte, toxin, inhibitor or fouling agent. The sensor is regenerated by removal of the stimulus (or, not shown, exposure of a second stimulus-interactive molecule to a second stimulus).

A schematic illustration is provided in FIG. 16 of the use of a conjugate of a stimulus-interactive molecule and an interactive molecule such as an enzyme, antibody, or receptor protein as an environmental sensor. The sensor protein is protected and inactive until exposed to a stimulus. The thetic "core" streptavidin gene designed for bacterial expression. The streptavidin gene was cut between the Kpn I and Xba I sites, and a synthetic cassette introducing the desired Asn to Cys codon change was subsequently ligated between the sites. The N49C streptavidin mutant sequence was confirmed by automated dideoxy sequencing and subclones into pET 11 (Novagen, Madison, Wis.) for expression in $E.$ $coli$ strain BL21(DE3). The over-expressed protein was refolded using protocols of Stayton, supra, with the addition of 0.5 mM DTT to maintain the thiol oxidation state.

PNIPAAm with one thiol-reactive end group/chain was synthesized in two steps. In the first step, PNIPAAm polymer with —OH end groups was prepared by chain transfer polymerization using 2-mercaptoethanol as a chain transfer agent and 2,2'-azoisobutyronitrile as initiator. The MW (Mn) was measured using an osmometer to be 3800. In the second step, the —OH end groups were reacted with divinyl sulfone (5 mole % excess) in the presence of triethylamine (5 mole % excess). The polymer was recovered by precipitation in ethyl ether. The product showed characteristic vinyl sulfone peaks in the proton NMR spectrum (in $d_6$-DMSO) at 6.21 ppm (two H=$CH_2$ and 6.97 ppm (one H=—$SO_2$CH=).

The conjugation of the vinyl sulfone-poly(NIPAAm) to the N49C streptavidin was performed at pH 7.0 in PBS, with Tris(2-carboxyethyl)phosphine (TCEP) as a disulfide reducing agent (Burns et al., $J.$ $Org.$ $Chem.$ 56:2648–2650 (1991)), using a large excess of polymer (molar ratio of polymer:protein of 50:1). The polymer-protein conjugate was separated from unreacted protein by thermal precipitation of the poly(NIPAAm) and the conjugate at 37° C. Characterization by GPC and polyacrylamide gel electrophoresis (SDS-PAGE) demonstrated that all of the streptavidin purified in this manner was conjugated to poly (NIPAAm).

Figure 10:
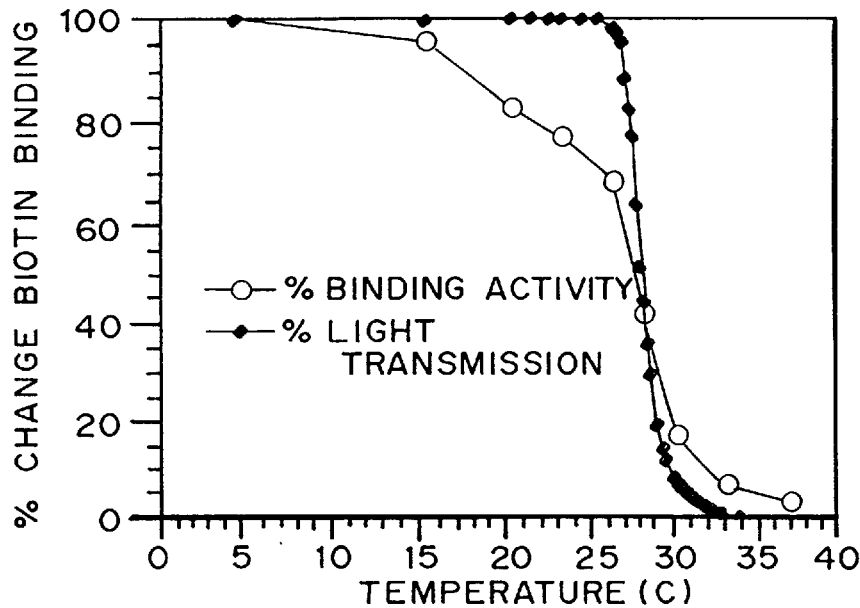
FIG. 10 shows the relationship between the thermal dependence of the biotin-binding activity and the cloud point behavior of free poly(NIPAAm). The activity plot represents the % change in the biotin binding activity at the respective temperatures relative to 4° C. (100% bound). The cloud point behavior of the free polymer is plotted as % change in the light absorbance from 4° C. (100%) to the upper temperature at 37° C.

The poly(NIPAAm)-streptavidin conjugate was next immobilized on a biotinylated microporous membrane. Hydrophilic poly(vinylidene difluoride) (PVDF) membranes (Millipore, Bedford, Mass.) were first coated with polyethyleneimine (PEI), a primary amine-containing polymer, by physical adsorption of 50 kD PEI. A biotinylated surface was then prepared by conjugating the N-hydroxy succinimidyl ester of biotin to the PEI primary amine groups. The N49C streptavidin-poly(NIPAAm) conjugate was adsorbed by affinity binding of the streptavidin to phase behavior of the conjugated poly(NIPAAm) was obtained by measuring the % blockage of biotin association as a function of temperature between 4° C. and 37° C. FIG. 10 shows the effect of temperature on the ability of the poly (NIPAAm) chain conjugated to streptavidin to block the biotin binding site as it collapses (open circles), and the phase separation of free poly (NIPAAm) in identical buffer conditions as measured by decreasing light transmission (closed circles). It can be seen that both curves decrease across the same temperature range, with nearly identical midpoints. The initiation of blocking activity of the conjugate precedes the sharp cloud point transition of the free polymer, which likely reflects the initiation of the gradual collapse of individual poly(NIPAAm) chains at the biotin binding pockets. The free poly(NIPAAm) chains in solution, on the other hand, must reach a critical level of hydrophobicity as they release bound water, at which condition they will aggregate together and precipitate, which leads to a cooperative phase separation and the observed sharp reduction in light transmission. The initial collapse of the poly (NIPAAm) chains that precedes the critical aggregation point can be seen in the activity assay for the conjugate as the early blocking of biotin binding around 20–25° C. (which is well below the LCST of the free polymer in solution).

Thus, these results demonstrate that the blocking of streptavidin-biotin association directly correlates with the collapse of the poly(NIPAAm) random coil, indicating that the affinity recognition process is indeed being controlled by narrow environmental control of the size of the polymer coil conjugated specifically at the N49C streptavidin binding pocket. The site-specific conjugation of such phase reversible polymers to genetically-engineered recognition proteins thus provides very sensitive environmental control of the ligand-protein recognition process.

EXAMPLE 2

Preparation of a temperature-sensitive chain with two reactive end groups.

Figure 13:
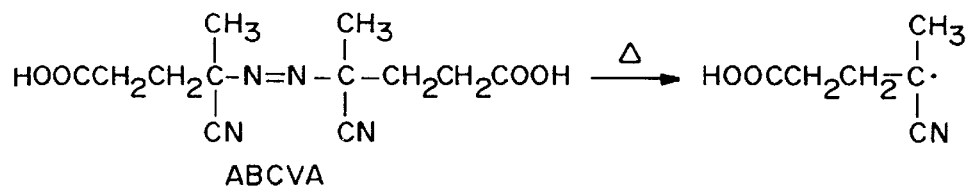
FIG. 13 illustrates the synthesis of PNIPAAm with two carboxyl terminal groups using a two-component iniferter system.
Figure 13:
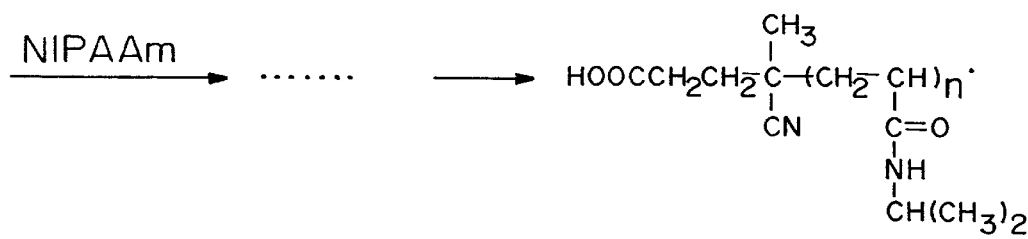
Figure 13:
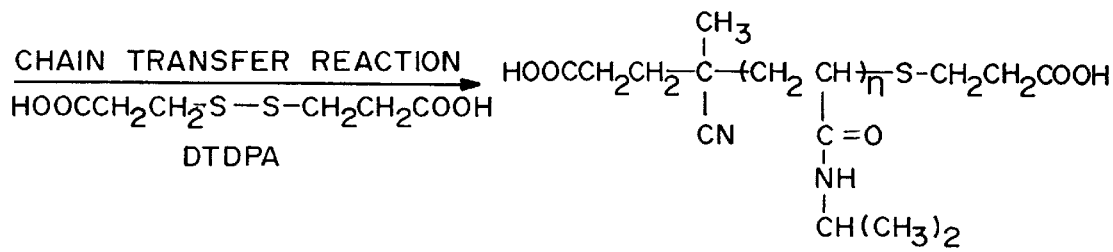

PNIPAAm with two carboxyl terminal groups can be synthesized by using a two-component iniferter system. The chemistry, shown in FIG. 13, was developed as described in: Otsu, T., et al. (1992) *Eur. Polym. J.*, 28, 1325–1329. In the system, 4,4-azobis-4-cyanovaleric acid (ABCVA) was used as an initiator and 3,3'-dithiodipropionic acid (DTDPA) was used as a chain transfer agent.

N-isopropylacrylamide (NIPAAm, Eastman Kodak, Rochester, N.Y., USA) was purified by recrystallization from n-hexane. ABCVA (PFATZ & BAUER INC.) and DTDPA (Aldrich) were used as received.

11.3 g of monomer, NIPAAm, plus 0.1 mole % ABCVA and 5 mole % DADPA were dissolved in 50 ml of DMF. The solution was degassed by freezing and evacuating and thawing three times and then sealed. Polymerization was carried out at 60° C. for 3 hours. The polymer was collected by precipitation in diethyl ether and dried in vacuum. The molecular weight of the polymer was determined by vapor pressure osmometry (VPO, model OSV111 from Knauer, German) and the content of carboxyl groups of the polymer was determined by back titration.

EXAMPLE 3

Synthesis of a pH- and temperature-sensitive polymer and its LCST behavior at two pHs.

N-isopropylacrylamide (NIPAAm, Eastman Kodak, Rochester, USA) was purified by recrystallization from n-hexane and dried in vacuum. Dimethylformamide (DMF) and 2-mercapthoethanol (ME) were used without further purification. Acrylic acid (AAc, Aldrich, Milwaukee, USA) was redistilled in vacuo before use. 2-2' Azoisobutyronitrile (AIBN, J. T. Baker, Phillisburg, USA) was recrystallized from methanol. All other reagents used were of analytical grade.

Poly(NIPAAm/AAc) with a terminal hydroxyl group was synthesized by chain transfer free radical copolymerization of NIPAAm (16.95 g, 150 mmol) and AAc (0.108 g, 1.5 mmol) in DMF (60 ml) at 60° C. for 20 min using a chain transfer agent, ME (0.478 g, 6 mmol) and a free radical initiator, AIBN (0.246 G, 1.5 mmol). Product was obtained by precipitating the reaction solution into diethyl ether, filtered through a sintered glass filter, washed repeatedly with diethyl ether, and dried in vacuum at 40° C. for 24 h. The synthesis is shown in FIG. 14.

The temperature and pH sensitive behaviors of copolymer were studied by spectophotometrically determining the turbidity of the polymer solution (2.0 mg/ml) at various temperatures and pHs at a fixed wavelength (500 nm). Citric-phosphate buffers were employed for investigating the effect of pH on the temperature sensitive behaviors of the copolymer. Ionic strength of the buffer solutions was adjusted by adding NaCl. The temperature at 10% absorbance of the polymer solution was defined as the LCST.

Figure 15:
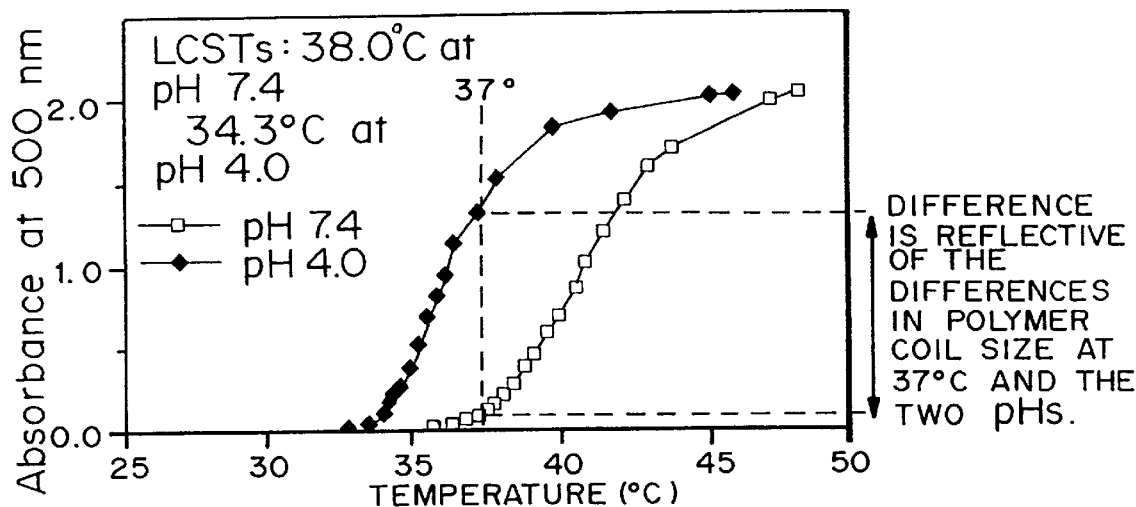
FIG. 15 is a graph of the absorbance vs temperature of 0.2% solution of poly (NIPAAm/AAc) in citric+phosphate buffers at pH 4.0 and 7.4. Ionic strengths of buffer solutions were adjusted by adding NaCl. Molar ratios of NIPAAm/AAc/2-ME/AIBN: 100/1/4/1, polymerization time: 20 min, polymerization temperature 60° C.

FIG. 15 shows the absorbance vs temperature of 0.2% solution of poly (NIPAAm/AAc) in citric+phosphate buffers at pH 4.0 and 7.4. Ionic strengths of buffer solutions were adjusted by adding NaCl. Molar ratios of NIPAAm/AAc/2-ME/aibn: 100/1/4/1, polymerization time: 20 min, polymerization temperature: 60° C.

Although the foregoing invention has been described in some detail by way of illustration and example for purposes of clarity of understanding, it will be obvious that certain changes and modifications may be practiced within the scope of the appended claims.

We claim:

1. A synthetic stimulus responsive conjugate comprising:
   an affinity interactive polymeric component capable of specifically binding to a target selected from the group consisting of a protein, peptide, polysaccharide, oligosaccharide, and glycoprotein; and
   a stimulus responsive polymeric component modulating the binding of the affinity interactive polymeric component to the target in response to a stimulus altering the conformation of the stimulus responsive polymeric component selected from the group consisting of light, pH, ions, ionic strength, electric field and solvents,
   wherein the components are coupled directly or indirectly by means of a spacer or linker at a linkage site selected from the group consisting of (a) just outside the binding site of the molecule, (b) at a selected distance away from the binding site, (c) just inside the binding site, (d) deep inside the binding pocket, and (e) at an allosteric site distant from the binding site, wherein the binding of the affinity interactive polymeric component to the target does not change in response to the stimulus except when conjugated to the stimulus responsive polymeric component.

2. The conjugate of claim 1 wherein the stimulus responsive component is capable of modulating the binding of the affinity interactive component to the target in response to a change in pH.

3. The conjugate of claim 1 wherein the affinity interactive component is a protein or a peptide.

4. The conjugate of claim 3 wherein the affinity interactive component is selected from the group consisting of an antibody, antigen, cell membrane receptor, a ligand capable of binding to a cell membrane receptor, an enzyme, an enzyme substrate, and a cofactor.

5. The conjugate of claim 1 wherein the target is selected from the group consisting of an antibody, antigen, cell membrane receptor, a ligand capable of binding to a cell membrane receptor, an enzyme, an enzyme substrate, and a cofactor.

6. The conjugate of claim 1 wherein the affinity interactive component comprises a molecule selected from the group consisting of a therapeutic agent, a diagnostic agent, and a catalytic agent.

7. The conjugate of claim 1 wherein the affinity interactive region comprises a therapeutic agent selected from the group consisting of an antibiotic agent, an anti-inflammatory agent, an anti-cancer agent, an anti-viral agent and an anti-enzyme agent.

8. The conjugate of claim 1 wherein the stimulus responsive conjugate is immobilized upon a surface or within a hydrogel.

9. The conjugate of claim 1 comprising a spacer between the affinity interactive component and the stimulus responsive component.

10. A method for making a synthetic stimulus responsive conjugate comprising:
coupling an affinity interactive polymeric component capable of specifically binding to a target with a stimulus responsive polymeric component modulating the binding of the affinity interactive component to the target in response to a stimulus,
wherein the affinity interactive polymeric is selected from the group consisting of a protein, peptide, polysaccharide, oligosaccharide, and glycoprotein and the stimulus responsive polymeric component modulates the binding of the affinity interactive polymeric component to the target in response to a stimulus altering the conformation of the stimulus responsive polymeric component which is selected from the group consisting of light pH, ions, ionic strength, electric field and solvents,
wherein the two polymeric components are coupled at a linkage site selected from the group consisting of (a) just outside the binding site of the molecule, (b) at a selected distance away from the binding site, (c) just inside the binding site, (d) deep inside the binding pocket, and (e) at an allosteric site distant from the binding sites, wherein the binding of the affinity interactive polymeric component to the target does not chance in response to the stimulus except when conjugated to the stimulus responsive polymeric component.

11. The method of claim 10 wherein the stimulus responsive component is capable of modulating the binding of the affinity interactive component to the target in response to a change in pH.

12. The method of claim 10 wherein the affinity interactive component is a protein or a peptide.

13. The method of claim 12 wherein the affinity interactive component is selected from the group consisting of an antibody, antigen, cell membrane receptor, a ligand capable of binding to a cell membrane receptor, an enzyme, an enzyme substrate and a cofactor.

14. The method of claim 10 wherein the target is selected from the group consisting of an antibody, antigen, cell membrane receptor, a ligand capable of binding to a cell membrane receptor, an enzyme, an enzyme substrate and a cofactor.

15. The method of claim 10 wherein the affinity interactive component comprises a molecule selected from the group consisting of a therapeutic agent, a diagnostic agent, and a catalytic agent.

16. The method of claim 10 wherein the affinity interactive component comprises a therapeutic agent selected from the group consisting of an antibiotic agent, an anti-inflammatory agent, a catalytic agent, an anti-cancer agent, an anti-viral agent, and an anti-enzyme agent.

17. The method of claim 10 wherein the target comprises a molecule selected from the group consisting of a therapeutic agent, a diagnostic agent, and a catalytic agent.

18. The method of claim 10 wherein the stimulus responsive conjugate is immobilized upon a surface or within a hydrogel.

19. The method of claim 18 wherein the stimulus responsive conjugate is immobilized on a solid surface and wherein the method further comprises separating the target from a mixture using the stimulus responsive conjugate in a separation method selected from the group consisting of low pressure chromatography, high performance liquid chromatography, affinity precipitation, membrane separation, two phase separation and immunoadsorption separation.

20. The method of claim 18 wherein the stimulus responsive conjugate immobilized upon a surface is provided within a sensor device for the detection of the target, the method further comprising detecting the target in a sample with the sensor.

21. The method of claim 10 wherein the components are coupled by complexation.

22. The method of claim 10 wherein the components are coupled by covalent linkage.

* * * * *

UNITED STATES PATENT AND TRADEMARK OFFICE
CERTIFICATE OF CORRECTION

PATENT NO.    : 5,998,588
DATED         : December 7, 1999
INVENTOR(S)   : Allan S. Hoffman and Patrick S. Stayton It is certified that error appears in the above-identified patent and that said Letters Patent is hereby corrected as shown below:

<u>Column 1,</u>
Line 2, insert:
-- STATEMENT REGARDING FEDERALLY SPONSORED RESEARCH OR DEVELOPMENT
The U.S. government has certain rights in this invention by virtue of National Science Foundation grant no. BCS 9101716 to Patrick S. Stayton and Allan S. Hoffman. --

Signed and Sealed this

First Day of July, 2003

JAMES E. ROGAN
*Director of the United States Patent and Trademark Office*